United States Patent
Lahann

(10) Patent No.: US 8,241,651 B2
(45) Date of Patent: *Aug. 14, 2012

(54) MULTIPHASIC BIOFUNCTIONAL NANO-COMPONENTS AND METHODS FOR USE THEREOF

(75) Inventor: Joerg Lahann, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 915 days.

This patent is subject to a terminal disclaimer.

(21) Appl. No.: 11/763,842

(22) Filed: Jun. 15, 2007

(65) Prior Publication Data

US 2007/0237800 A1    Oct. 11, 2007

Related U.S. Application Data

(63) Continuation-in-part of application No. 11/272,194, filed on Nov. 10, 2005, now Pat. No. 7,767,017.

(60) Provisional application No. 60/651,288, filed on Feb. 9, 2005, provisional application No. 60/626,792, filed on Nov. 10, 2004, provisional application No. 60/814,706, filed on Jun. 16, 2006.

(51) Int. Cl.
*H05F 3/00* (2006.01)
*B05D 1/04* (2006.01)
*B29C 67/00* (2006.01)
*A61J 3/00* (2006.01)

(52) U.S. Cl. ............ 424/422; 106/401; 264/9; 264/484; 424/489; 977/906; 204/164

(58) Field of Classification Search ........................ None
See application file for complete search history.

(56) References Cited

U.S. PATENT DOCUMENTS

| | | | |
|---|---|---|---|
| 3,060,429 | A | 10/1962 | Winston |
| 4,621,268 | A | 11/1986 | Keeling et al. |
| 5,560,543 | A | 10/1996 | Smith et al. |
| 5,741,138 | A | 4/1998 | Rice et al. |

(Continued)

FOREIGN PATENT DOCUMENTS

EP    1809719    7/2007

(Continued)

OTHER PUBLICATIONS

Barrero, A. et al., "Micro- and Nanoparticles via Capillary Flows", Annu. Rev. Fluid Mech., vol. 39, pp. 89-106 (2007).

(Continued)

*Primary Examiner* — Melvin C Mayes
*Assistant Examiner* — Yun Qian
(74) *Attorney, Agent, or Firm* — Harness, Dickey & Pierce, P.L.C.

(57) ABSTRACT

Multiphasic nano-components (MPNs) having at least two phases and at least one active ingredient are provided. The MPNs can be used in various methods for medical diagnostics or with pharmaceutical, personal care, oral care, and/or nutritional compositions, for example, in oral care, hair, or skin products. The MPNs can be designed to have targeted delivery within an organism, while providing controlled release systems or combining incompatible active ingredients. Further, the MPNs can be used as biomedical coatings (such as anti-microbial coatings), or anti-corrosive coatings, bioimaging probes with combined diagnostic and therapeutic use, and fragrance release systems, among others. The MPNs can be formed by electrified jetting of polymers.

18 Claims, 6 Drawing Sheets

U.S. PATENT DOCUMENTS

| | | | |
|---|---|---|---|
| 5,813,614 A | 9/1998 | Coffee | |
| 6,007,845 A * | 12/1999 | Domb et al. | 424/501 |
| 6,063,365 A | 5/2000 | Shefer et al. | |
| 6,107,102 A | 8/2000 | Ferrari | |
| 6,132,702 A | 10/2000 | Witt et al. | |
| 6,252,129 B1 | 6/2001 | Coffee | |
| 6,267,724 B1 | 7/2001 | Taylor | |
| 6,306,993 B1 | 10/2001 | Rothbard et al. | |
| 6,391,471 B1 | 5/2002 | Hiraoka et al. | |
| 6,491,902 B2 | 12/2002 | Shefer et al. | |
| 6,548,264 B1 | 4/2003 | Tan et al. | |
| 6,589,562 B1 | 7/2003 | Shefer et al. | |
| 6,669,961 B2 | 12/2003 | Kim et al. | |
| 6,685,921 B2 | 2/2004 | Lawlor | |
| 6,703,235 B2 | 3/2004 | Luebke et al. | |
| 6,766,817 B2 | 7/2004 | da Silva et al. | |
| 6,811,090 B2 | 11/2004 | Yogi et al. | |
| 6,825,161 B2 | 11/2004 | Shefer et al. | |
| 6,918,404 B2 | 7/2005 | Dias da Silva et al. | |
| 7,066,586 B2 | 6/2006 | da Silva et al. | |
| 7,413,868 B2 | 8/2008 | Kauvar et al. | |
| 7,767,017 B2 | 8/2010 | Lahann et al. | |
| 2006/0201390 A1* | 9/2006 | Lahann et al. | 106/401 |
| 2007/0054119 A1 | 3/2007 | Garstecki et al. | |
| 2007/0112180 A1 | 5/2007 | Gray et al. | |
| 2007/0167340 A1 | 7/2007 | Barthel et al. | |
| 2007/0231355 A1 | 10/2007 | Quadir et al. | |
| 2008/0242774 A1* | 10/2008 | Lahann et al. | 524/99 |
| 2010/0015447 A1* | 1/2010 | Lahann et al. | 428/403 |
| 2010/0038830 A1 | 2/2010 | Lahann et al. | |

FOREIGN PATENT DOCUMENTS

| | | |
|---|---|---|
| JP | 2004-505761 | 2/2004 |
| JP | 2005504090 | 2/2005 |
| JP | 2008520407 | 6/2008 |
| WO | WO 02/13786 | 2/2002 |
| WO | WO 03/026611 | 4/2003 |
| WO | WO 2006/003403 | 1/2006 |
| WO | WO 2006/137936 | 12/2006 |
| WO | WO 2007/149310 | 12/2007 |
| WO | WO 2009/055693 | 4/2009 |
| WO | WO 2009/151421 | 12/2009 |
| WO | WO 2010/011641 | 1/2010 |
| WO | WO 2010/127119 | 11/2010 |

OTHER PUBLICATIONS

Cayre, O., et al., "Fabrication of Asymmetrically Coated Colloid Particles by Microcontact Printing Techniques", J. Mater. Chem., vol. 13, pp. 2445-2450 (2003).

Cayre, O., et al., "Fabrication of Dipolar Colloid Particles by Microcontact Printing", Chem. Commun., pp. 2296-2297 (2003).

Erhardt, R., et al., "Amphiphilic Janus Micelles With Polystyrene and Poly(methacrylic acid) Hemispheres", J. Am. Chem. Soc., vol. 125, pp. 3260-3267 (2003).

Erhardt, R., et al., "Janus Micelles", Macromolecules, vol. 34, pp. 1069-1075 (2001).

Farokhzad, O. et al., "Nanoparticle-Aptamer Bioconjugates: A New Approach for Targeting Prostate Cancer Cells", Cancer Research, vol. 64, pp. 7668-7672 (2004).

Guo, K. et al., "Aptamer-based capture molecules as a novel coating strategy to promote cell adhesion", J. Cell. Mol. Med., vol. 9, No. 3, pp. 731-736 (2005).

Hicke, B. et al., "Tumor Targeting by an Aptamer", J. of Nuclear Med., vol. 47, No. 4, pp. 668-678 (2006).

Larsen, G., et al., "A Method for Making Inorganic and Hybrid (Organic/Inorganic) Fibers and Vesicles with Diameters in the Submicrometer and Micrometer Range via Sol-Gel Chemistry and Electrically Forced Liquid Jets", J. Am. Chem. Soc., vol. 125, pp. 1154-1155 (2003).

Loscertales, I. et al., "Electrically Forced Coaxial Nanojets for One-Step Hollow Nanofiber Design", J. Am. Chem. Soc., vol. 126, pp. 5376-5377 (2004).

Loscertales, I. et al., "Production of complex nano-structures by electro-hydro-dynamics", Mater. Res. Soc. Symp. Proc., vol. 860E, pp. LL5.9.1-LL5.9.6 (2005).

Marin, A. et al., "Simple and Double Emulsions via Coaxial Jet Electrosprays", The Amer. Phys. Soc., vol. 98, pp. 014502-1 to 014502-4 (2007).

Paunov, V., et al., "Novel Technique for Preparation of Dipolar Microparticles by Polymerization of Polarised Emulsions", Abstract Central, 1 page (undated).

Perro, A., et al., "Design and Synthesis of Janus Micro- and Nanoparticles", The Royal Soc. of Chem., vol. 15, pp. 3745-3760 (2005).

Roh, K., et al., "Biphasic Janus Particles with Nanoscale Anisotrophy", Nature Materials, vol. 4, pp. 759-763 (2005).

Roh, K., et al., "Triphasic Nanocolloids", J. Am. Chem. Soc., vol. 128, pp. 6796-6797 (2006).

Uhrich, K. et al., "Polymeric Systems for Controlled Drug Release", Chem. Rev., vol. 99, pp. 3181-3198 (1999).

Berkland C., et al., "Controlling surface nano-structure using flow-limited field-injection electrostatic spraying (FFESS) of poly(D,L-lactide-co-glycolide)," Biomaterials, vol. 25, No. 25, pp. 5649-5658 (Nov. 2004).

Bhaskar, S. et al., "Spatioselective Modification of Bicompartmental Polymer Particles and Fibers via Huisgen 1,3-Dipolar Cycloaddition," Macromol. Rapid Commun., vol. 29, No. 20, pp. 1655-1660 (Oct. 22, 2008). First published online Sep. 12, 2008.

Binks, B. P. et al., "Particles Adsorbed at the Oil-Water Interface: A Theoretical Comparison between Spheres of Uniform Wettability and "Janus" Particles," Langmuir, vol. 17, pp. 4708-4710 (2001).

Casagrande, C. et al., "Janus Beads: Realization and Behaviour at Water/Oil Interfaces," Europhys. Lett., vol. 9, No. 3, pp. 251-255 (1989).

Cloupeau, M. et al., "Electrohydrodynamic spraying functioning modes—a critical—review," J. Aerosol Sci., vol. 25, No. 6, pp. 1021-1036 (1994).

Cloupeau, M. et al., "Electrostatic spraying of liquids—Main functioning modes, " J. Electrostatics, vol. 25, pp. 165-184 (1990).

De La Mora, J. F. et al., "The current emitted by highly conducting Taylor cones," J. Fluid Mech., vol. 260, pp. 155-184 (1994).

Fridrikh, S. V. et al., "Controlling the Fiber Diameter during Electrospinning," Phys. Rev. Lett., vol. 90, No. 14, pp. 144502-1 to 144502-4 (2003).

Gomez, A. et al., "Charge and fission of droplets in electrostatic sprays," Phys. Fluids, vol. 6, No. 1, pp. 404-414 (1994).

Gunatillake, P. et al., "Biodegradable Synthetic Polymers for Tissue Engineering," European Cells and Materials, vol. 5, pp. 1-16 (2003).

Gupta, P. et al, "Some investigations on the fiber formation by utilizing a side-by-side bicomponent electrospinning approach," Polymer, vol. 44, pp. 6353-6359 (2003).

Hohman, M. M. et al., "Electrospinning and electrically forced jets. II. Applications," Physics of Fluids, vol. 13, No. 8, pp. 2221-2236 (2001).

Hohman, M. M. et al., "Electrospinning and electrically forced jets. I. Stability Theory," Physics of Fluids, vol. 13, No. 8, pp. 2201-2220 (2001).

Huang, Z. et al., "A review on polymer nanofibers by electrospinning and their applications in nanocomposites," Comp. Sci. Tech., vol. 63, pp. 2223-2253 (2003).

International Search Report and Written Opinion of the International Searching Authority issued on Mar. 8, 2010 in cross-referenced matter PCT/US2009/051238 (W02010/011641).

International Search Report and Written Opinion of the International Searching Authority issued on Mar. 11, 2009 in cross-referenced matter PCT/US2008/007372 (WO 2009/151421).

International Search Report and Written Opinion of the International Searching Authority issued on Jul. 23, 2009 in cross-referenced matter PCT/US2008/081145 (WO 2009/055693).

International Search Report and Written Opinion of the International Searching Authority issued on Jul. 21, 2008 in corresponding related PCT International Application PCT/US2007/014028 (WO 2007/149310).

Kazemi, A., et al., "Environmentally Responsive Core/Shell Particles via Electrohydrodynamic Co-jetting of Fully Miscible Polymer Solutions," Small, vol. 4, No. 10, pp. 1756-1762 (2008).

Lahann, J. et al., "Biphasic nanoparticles made by electrified jetting," 2005 APS March meeting, (Mar. 22, 2005).

Loscertales, I. et al., "Micro/nano Encapsulation via Electrified Coaxial Liquid Jets," Science, vol. 295, pp. 1695-1698 (2002).

Nie, Z. et al., "Janus and Ternary Particles Generated by Microfluidic Synthesis: Design, Synthesis, and Self-Assembly," J. Am. Chem. Soc., vol. 128, pp. 9408-9412 (2006).

Nisisako, T. et al., "Synthesis of Monodisperse Bicolored Janus Particles with Electrical Anisotropy Using a Microfluidic Co-Flow System," Adv. Mater., vol. 18, pp. 1152-1156 (2006).

Non-Final Office Action for U.S. Appl. No. 12/137,121 (U.S. Pub. No. 2008/0242774) dated May 25, 2010.

Non-Final Office Action for U.S. Appl. No. 12/257,945 (U.S. Pub. No. 2010/0038830) dated May 14, 2010.

Non-Final Office Action for U.S. Appl. No. 12/506,712 (U.S. Pub. No. 2010/0015447) dated Sep. 22, 2010.

Non-Final Office Action for U.S. Appl. No. 12/137,121 (U.S. Pub. No. 2008/0242774) dated Feb. 3, 2010.

Notice of Rejection issued on Jul. 27, 2010 in related matter Japanese Patent Publication JP 2007-540191. English translation provided by Kashiwabara International Patent Bureau.

Palm, L. et al., "An Optical Method for Measuring Drop Flight Stability in a Continuous Ink Jet," Journal for Imaging Science and Technology, vol. 41, No. 1 (Jan./Feb. 1997).

Response filed on Mar. 3, 2010 to Non-Final Office Action dated Feb. 3, 2010 for U.S. Appl. No. 12/137,121 (U.S. Pub. No. 2008/0242774).

Response filed on Nov. 12, 2010 to Non-Final Office Action dated May 14, 2010 for U.S. Appl. No. 12/257,945 (U.S. Pub. No. 2010/0038830).

Response filed on Nov. 18, 2010 to Non-Final Office Action dated May 25, 2010 for U.S. Appl. No. 12/137,121 (U.S. Pub. No. 2008/0242774).

Response filed on Oct. 19, 2010 to Non-Final Office Action dated Sep. 22, 2010 for U.S. Appl. No. 12/506,712 (U.S. Pub. No. 2010/0015447).

Rodenberg, E.J. et al., "Peptides Derived from Fibronectin Type III Connecting Segments Promote Endothelial Cell Adhesion but Not Platelet Adhesion: Implications in Tissue-Engineered Vascular Grafts," Tissue Engineering, vol. 13, No. 11 pp. 2653-2665 (2007).

Rosell-Llompart, J. et al., "Generation of Monodisperse Droplets 0.3 to 4 µm in Diameter from Electrified Cone-Jets of Highly Conducting and Viscous Liquids," J. Aerosol Sci., vol. 25, No. 6, pp. 1093-1119 (1994).

Shepherd, R. F. et al., "Microfluidic Assembly of Homogeneous and Janus Colloid-Filled Hydrogel Granules," Langmuir, vol. 22, pp. 8618-8622 (2006).

Shin, Y. M. et al., "Electrospinning: A whipping fluid jet generates submicron polymer fibers," Appl. Phys. Lett, vol. 78, No. 8, pp. 1149-1151 (2001).

Sun, Q. et al., "Design of Janus Nanoparticles with Atomic Precision," 2008 APS March meeting (Mar. 13, 2008).

Sun, Z. C. et al., "Compound Core-Shell Polymer Nanofibers by Co-Electrospinning," Adv. Mater., vol. 15, No. 22, pp. 1929-1932 (2003).

Takei, H. et al., "Gradient Sensitive Microscopic Probes Prepared by Gold Evaporation and Chemisorption on Latex Spheres," Langmuir, vol. 13, No. 7, pp. 1865-1868 (1997).

Wako Pure Chemical Industries, Ltd., Biodegradable Polymers (PLA-PLGA) http://www.wako-chem.co.jp/specialty/plga/index.htm.

Zeleny, J., "Instability of electrified liquid surfaces," Phys. Rev., vol. 10, No. 1, pp. 1-6 (1917).

\* cited by examiner

MULTIPHASIC BIOFUNCTIONAL NANO-COMPONENTS AND METHODS FOR USE THEREOF

CROSS-REFERENCE TO RELATED APPLICATIONS

This application claims the benefit of U.S. Provisional Application No. 60/814,706, filed on Jun. 16, 2006. This application is also a continuation-in-part of U.S. patent application Ser. No. 11/272,194 filed on Nov. 10, 2005, now U.S. Pat. No. 7,767,017, which claims priority to U.S. Provisional Application Nos. 60/626,792 filed on Nov. 10, 2004 and 60/651,288 filed on Feb. 9, 2005. The disclosures of each of the respective applications above are incorporated herein by reference in their respective entireties.

FIELD

The present disclosure relates to the fabrication of nanoparticles and, more particularly, to fabrication of polymer-based multiphasic nano-components (MPNs) for use as active ingredient delivery systems.

BACKGROUND

The statements in this section merely provide background information related to the present disclosure and may not constitute prior art.

Effective drug delivery is important for optimizing efficacy of active ingredients or active agents. Thus, pharmaceutical, nutraceutical, and cosmetic active ingredients/agents, for example, are optimally delivered and maintained near one or more target regions in an organism to expose the target tissue or cells to the desired active ingredients for a predetermined time and concentration. So-called "drug targeting" modifies the pharmacokinetics and biodistribution of active ingredients to provide the potential for increased efficacy, while minimizing intrinsic toxicity.

SUMMARY

In various aspects, a multiphasic nano-component is provided that comprises a first phase and at least one additional phase distinct from the first phase. The first phase and the at least one additional phase each have an exposed surface. Further, one or more of the first phase and the additional phase include a pharmaceutically and/or cosmetically acceptable polymer. Similarly, one or more of the first phase and the additional phase comprise an active ingredient.

In other aspects, the present disclosure provides a targeted delivery system. For example, a method is provided for delivering an active ingredient to an animal. The method comprises providing a pharmaceutically and/or cosmetically acceptable multiphasic nano-component comprising the active ingredient to an animal. The multiphasic nano-component comprises a moiety that binds to a target to promote release of an active ingredient near a target region associated the animal. The multiphasic nano-component comprises at least two distinct phases and comprises a pharmaceutically and/or cosmetically acceptable polymer and an active ingredient. Each phase has an exposed surface. In this manner, the active ingredient is released to the target region at an effective amount, thereby providing the desired benefit.

In yet other aspects, a method for treating and/or preventing a physiological and/or psychological condition in an animal, the method comprising: providing a pharmaceutically and/or cosmetically acceptable multiphasic nano-component to an animal. The multiphasic nano-component comprises at least two distinct phases, including a first phase comprising a first active ingredient and a distinct second phase comprising a second active ingredient. The first phase releases the first active ingredient at a first rate and the second phase releases the second active ingredient at a second rate differing from the first rate. Thus, the nano-component delivers an effective amount of each of the first and the second active ingredients to a target region of the animal in a system. The nano-component provides a delivery vehicle permitting a complex design for release kinetics to stage active ingredient release.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 1A, 1B, and 1C depict multiphasic nano-component compositions of the present disclosure having different respective volumes and surface areas of a first phase and a distinct second phase;

In FIG. 2A the apparatus forms discrete multiphasic nano-component solids and in FIG. 2B, the apparatus forms multiphasic nano-component fibers;

DETAILED DESCRIPTION

Figure 1C:
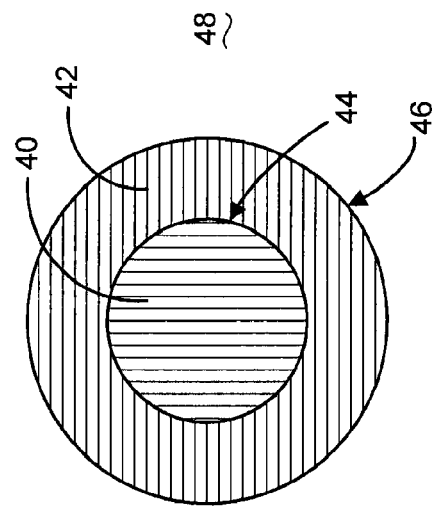

The following description is merely exemplary in nature and is not intended to limit the present disclosure, application, or uses.

In accordance with the present disclosure, new methods of forming and using multiphasic nano-components (e.g., nano-objects) capable of delivering active ingredients or biofunctional agents are provided. The teachings of the present disclosure pertain to developing active agent or active ingredient delivery for enhanced drug targeting, or enhanced efficacy of active ingredient via improved delivery to a target site in an organism.

Certain drug targeting techniques have suffered from challenges when such active ingredients are administered to target tissue or introduced into the circulatory system of a living organism, i.e., when used in vivo. For example, certain nano-scale particles have been observed to be rapidly cleared by the liver (Kupffer cells) and the spleen (macrophages). Further, in some examples, the active ingredients combined with nanoparticles may trigger or activate an immune system response in the organism. For example, it is believed that certain nanoparticles (for example, certain nanoparticles having an average diameter above 200 nm) activate the complement system of mammalian immune systems. Different sub-types of macrophages recognize and rapidly clear invading particulates, such as the foreign drug delivery vehicles, in various mammals. In addition, the pre-adsorption of blood-borne proteins often facilitates recognition by macrophages. Thus, drug targeting can be more effective if the carrier and delivery systems for such active ingredients are improved.

By way of background, drug targeting is generally classified into two classes, passive and active drug targeting. Passive drug targeting strategies take advantage of pathophysiological or anatomical properties of an organism, as where active strategies often involve selective affinity of a drug construct to permit recognition of a target (e.g., a specific cell, tissue, or organ). For example, a targeting moiety, such as an antibody, a peptide, a ligand, or an aptamer, is conjugated with an active ingredient itself or with a nanosystem (nanoparticles having at least one dimension less than about 1 μm or 1,000 nm, such as a nanoparticle, a liposome, a polysome, micelles, dendrimer-drug conjugates and the like) loaded with an active therapeutic agent. In some cases, direct coupling between a drug and targeting moiety limits the coupling capacity, thus, the use of alternate drug delivery vehicles would be advantageous. In contrast to targeting moieties, such as liposomes and polysomes, the present disclosure provides multiphasic polymer-based nanoparticles having at least one therapeutic agent incorporated within the polymer matrix.

Thus, the present disclosure in various aspects provides improved active ingredient delivery via new delivery or carrier systems. In certain variations, the teachings of the present disclosure provide enhanced drug targeting or diagnostics, or enhanced efficacy of active ingredient delivery to a target site in an organism. The multiphasic nano-components of the disclosure have one or more moieties that interact with a target associated with the animal, for example circulating cells or an organism's immune system cells to be delivered to a target site or target region within an organism by attachment to designated target region cells. In other aspects, the target may be associated with the target region itself, for example, infected or cancerous tissues or medical device surfaces. In this regard, the multiphasic nano-components can be delivered to the targeted tissue, for example, the site of infection, cancer, arteriosclerosis, and the like, for highly targeted and specific delivery.

Figure 1A:
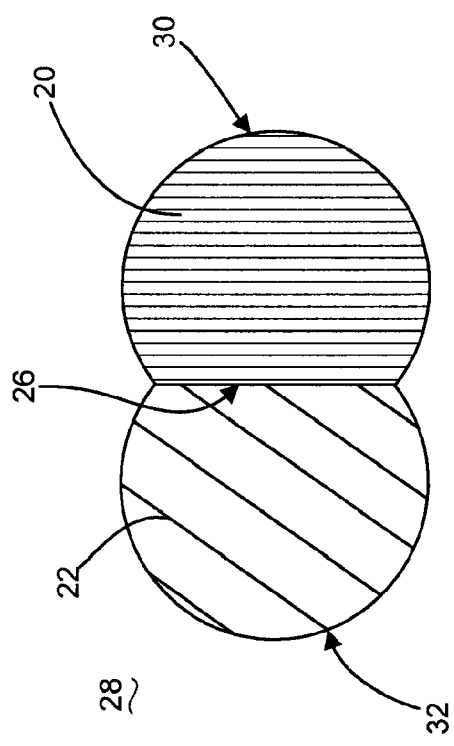
Figure 1B:
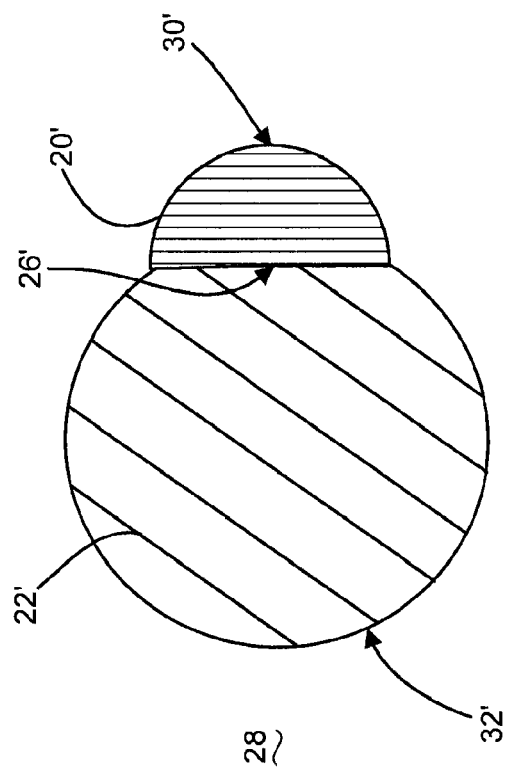

In various aspects, the present disclosure provides multiphasic components have a plurality of physically and/or compositionally distinct phases, such as shown in FIGS. 1A and 1B. While not shown here, three or more phases are contemplated by the present teachings as well. By the term "phase" it is meant that a portion of a component is chemically and/or physically distinct from another portion of the component. The multiphasic components according to the present teachings include a first phase and at least one phase that is distinct from the first phase. In certain aspects, the multiphasic components of the present disclosure include multiple distinct phases, for example three or more distinct phases. In some aspects, each respective phase occupies a spatially discrete region or compartment of the nano-component. In certain aspects, each respective phase of the multiphasic component is exposed to an external environment, thus providing exposure of the respective phase surfaces of the multiphasic component to an external environment. The exposure of each respective surface of each phase provides enhanced environmental interface and optimum diffusion or material transfer, resulting in increased bioavailability to target regions.

Configurations such as those shown in FIGS. 1A and 1B have three phase interfaces. In FIG. 1A, a first phase 20 and a second phase 22 share a first phase interface 26, where both the first phase 20 and second phase 22 occupy discrete spatial locations within the nano-component. First phase 20 also interacts with an external environmental medium 28 at a second phase interface 30. Lastly, the second phase 22 has a third phase interface with the medium 30 at a third phase interface 32. In FIG. 1B, a first phase 20' has a reduced surface area that is exposed to external medium 28 than the second phase 22'. However, such phases 20, 22' have a first, second, and third phase interface 26', 30', 32', like in FIG. 1A.

In another variation, to be described in more detail later, the multiphasic nano-component may have a core and shell configuration, as shown in FIG. 1C. Such a configuration only has two phase interfaces between a first phase 40 and a second phase 42. A first phase interface 44 between the first phase 40 and second phase 42 and a second phase interface 46 between second phase 42 and an external medium 48.

A "nano-component" is a material that has a variety of shapes or morphologies, however, generally has at least one spatial dimension that is less than about 10 μm (i.e., 10,000 nm). The term "nano-sized" or "nanometer-sized" is generally understood by those of skill in the art to mean less than about 10 μm (i.e., 10,000 nm), optionally less than about 2 μm (i.e., less than about 2,000 nm), optionally less than about 0.5 μm (i.e., 500 nm), and in certain aspects, less than about 200 nm. In certain aspects, a nano-component as used herein has at least one spatial dimension that is greater than about 1 nm and less than about 10,000 nm. In certain aspects, a nano-component has at least one spatial dimension of about 5 to about 5,000 nm. In some aspects, at least one spatial dimension of the nano-component is about 20 to about 2000 nm. In still other variations, nano-components have at least one spatial dimension of about 50 to about 500 nm.

In certain aspects, nano-components comprise materials in a solid phase or a semi-solid phase, although liquid phases are contemplated in certain variations. As mentioned above, the nano-components (used interchangeably with the term "nano-objects") may have a variety of geometries or morphologies, including, by way of non-limiting example, nano-components in the form of spheres, rectangles, polygons, disks, toroids, cones, pyramids, rods/cylinders, fibers, and the like. Nano-fibers generally have an elongated axial dimension that is substantially longer than the other dimensions of the nano-fiber. A "nano-particle" generally refers to a nano-component where all three spatial dimensions are nano-sized and less than or equal to several micrometers (e.g., less than about 10,000 nm).

In certain aspects, at least one phase of the multiphasic composition or nano-component comprises at least one active ingredient. As appreciated by one of skill in the art, the first phase and the second phase (or additional distinct phases) can optionally include active ingredients that are the same or different from one another. Thus, in certain aspects, the multiphasic component comprises a first phase having at least one active ingredient and a second distinct phase having at least one distinct active ingredient. For example, where a multiphasic composition comprises a first phase and a second distinct phase, the first phase comprises one or more first active ingredients and the second phase optionally likewise comprises one or more second active ingredients. When present, one or more of the first active ingredients of the first phase can be distinct from the one or more second active ingredients of the second phase. Thus, the first phase may comprise at least one distinct active ingredient from the second phase. Multiple phases of the composition may each respectively comprise at least one active ingredient and in some cases a plurality of distinct active ingredients. In other aspects, one or more of the distinct phases of the multiphasic nano-component may have a common active ingredient. The first and second phases (or additional phases) may contain one or more of the same active ingredients or different active ingredient cocktails (i.e., plurality or mixture of active ingredients). In certain aspects, the inventive multiphasic nano-components comprise multiple pharmaceutically active ingredients, such as exclusive or generic drugs, or combinations thereof.

In accordance with certain aspects of the present disclosure, the multiphasic nano-components ("MPNs") are suitable for use in a wide variety of biofunctional or bioactive applications. A "biofunctional" or "bioactive" substance refers to a chemical substance, such as a small molecule, macromolecule, metal ion, or the like, that causes an observable change in the structure, function, optical function, or composition of a cell when a cell is exposed to such a substance. Examples of observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, changes in optical properties, and the like. In certain aspects, the MPNs of the disclosure deliver active ingredients to a target, in some embodiments, to tissue or an organ of an organism. In other aspects, the MPNs provide binding to certain target regions in an organism to modify optical or physical properties to improve diagnostic procedures.

In various aspects, the nano-components according to the present teachings fulfill one or more of the following advantages. First, ability to design drug delivery vehicles for variation of active ingredient types and concentrations is realized, thus permitting in certain aspects, modular design of active ingredient delivery vehicles. Second, nano-components circulate and remain for long periods within the organism, thus avoiding immune system recognition and/or complement activation. Third, active targeting ability to deliver highly specific active ingredients to target tissues (for example, to a tumor site) to minimize systemic effects. This is particularly advantageous for chemotherapeutic treatments for cancer, where damage of attendant tissues can be minimized. Fourth, the ability to release multiple active ingredients with independently controllable release kinetics. Lastly, functional imaging that allows for distinguishing specific and non-specific binding.

In accordance with the present disclosure, advanced design of multiphasic nano-components capable of promoting active ingredient delivery to a localized region, such as cancer targeting, are provided. Such MPNs are robust enough to function in a biological environment having proteins and cells. In certain aspects, the MPNs, such as a biphasic nanoparticle, can serve as targeting elements for circulating blood cells carrying the active ingredient payload (e.g., chemotherapy drug) to the tumor. In accordance with the principles of the disclosure, the MPNs enable the engineering of spatially separated surface interactions, as well as the establishment of independent release kinetics for respective phases of the MPNs. These properties can improve active ingredient delivery.

Multiphasic nanoparticles can be made of a wide variety of materials, including inorganic and organic materials. Specifically, polymers, such as biodegradable or non-biodegradable polymers, biocompatible polymers, or natural polymers can be used. In one aspect, the first phase of the multiphasic nano-component comprises a first polymer and the second phase comprises a second polymer that is distinct from the first polymer. Thus, in certain aspects different polymers can be used in at least two phases of the multiphasic nanoparticle composition. In certain respects, different polymers used in the different phases of the MPN permit different active ingredient release kinetics, which can be useful in designing release of the active ingredient into the environment. Further, otherwise incompatible ingredients can be delivered simultaneously to a target region. One phase may contain a first active ingredient and a second phase may contain a second active ingredient that is otherwise incompatible with the first active ingredient. The first phase comprises materials compatible with the first component and the second phase similarly has materials compatible with the second component. Thus, a lipophilic or hydrophobic active ingredient can be included in one phase of the MPN and a hydrophilic active ingredient can be included in a second phase, however both the first and second active ingredients are delivered and bioavailable to target tissues. Similarly, a cationic active ingredient is contained in a first phase of the MPN and an anionic active ingredient is contained in a second phase of the MPN to provide both cationic and anionic active ingredients concurrently to the target tissue.

In various embodiments, at least one phase of the MPN comprises at least one polymer. In certain aspects, multiple phases of the MPN each comprise one or more polymers. In certain aspects, the polymers can also be modified by chemical or physical methods, such as cross-linking, heat treatment, photochemical treatment, and/or changes in the chemical or physical environment. In a certain aspects, the polymer modification occurs in a select portion or region of one or more of the multiple phases, or such polymer modification can occur to different degrees, potentially resulting in different materials or materials responses, as appreciated by one of skill in the art. Such polymer modification and/or treatment provides different release kinetics in certain aspects.

In certain aspects, the phases of the MPN dissolve or disintegrate at different rates. In this regard, the dissolution rate of the respective phases impacts the release rate of the active ingredient from each phase, thus providing control over the release kinetics and concentration of active ingredient to be delivered to target regions with each respective phase of the nano-component. As referred to herein, "dissolve" refers to physical disintegration, erosion, disruption and/or dissolution of a material. The phases may dissolve or disintegrate at different rates or have different solubilities (e.g., aqueous solubility) that impact the rate of active ingredient release. Each phase comprises one or more materials that dissolve or erode upon exposure to a solvent comprising a high concentration of water, such as serum, blood, bodily fluids, or saliva. In some variations, a phase may disintegrate into small pieces or may disintegrate to collectively form a colloid or gel. In some aspects, a phase of the MPN comprises a polymer that is insoluble or has limited solubility in water, but is dispersible in water, so that the polymer breaks down or erodes into small fragments. In other aspects, a polymer used in a phase of the MPN is insoluble in water, but swellable. In variations where a polymer does not fully break down during use, the polymer can be a water-repellant polymer or an aqueous-stable hydrophilic polymer, for example, certain types of cellulose. In various aspects, each phase of the MPN optionally comprises a combination of polymer materials.

Figure 2A:
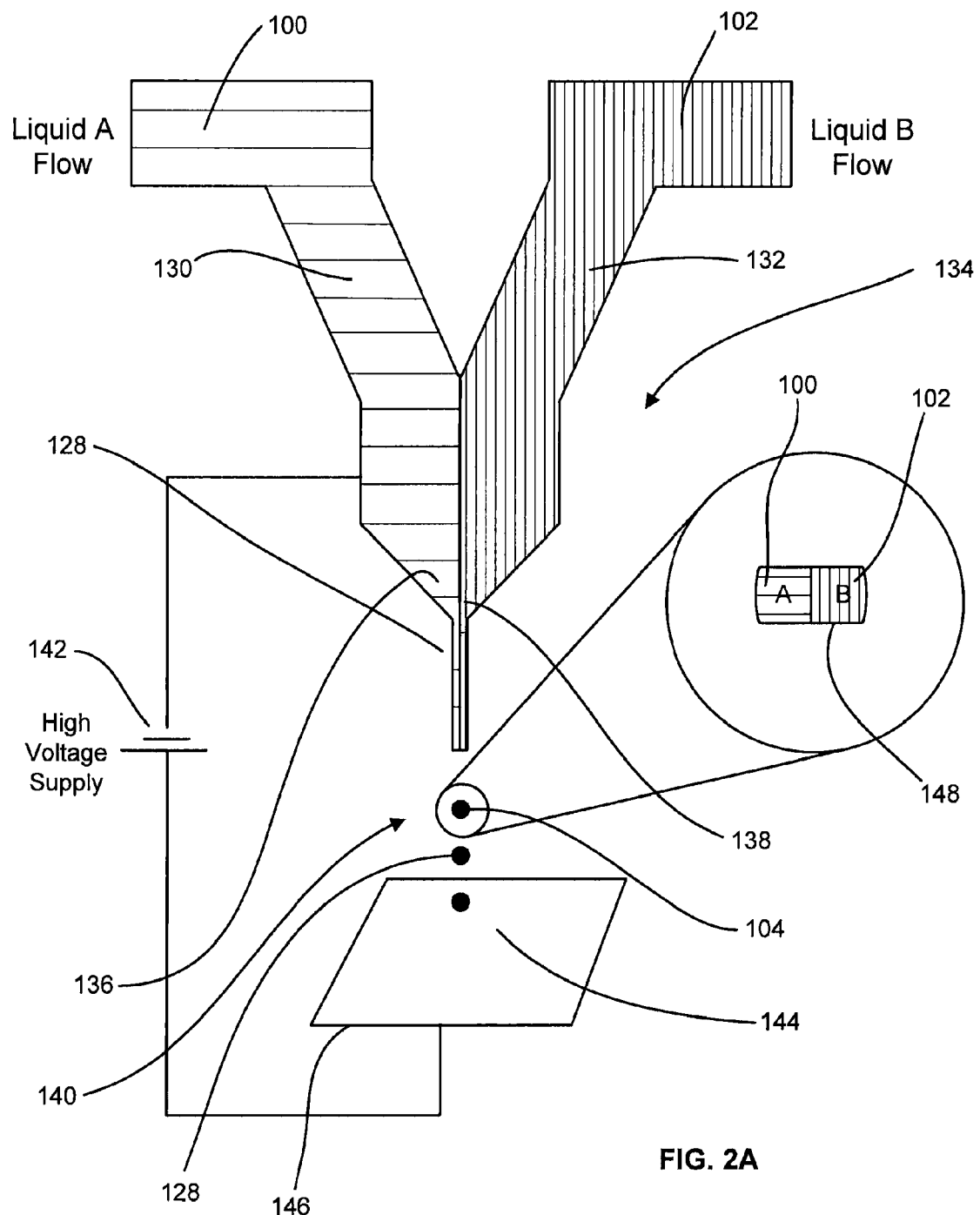
FIGS. 2A and 2B shows two exemplary apparatuses that form multiphasic nanoparticle compositions according to the present disclosure by electrically jetting fluid in a side-by-side configuration.
Figure 2B:
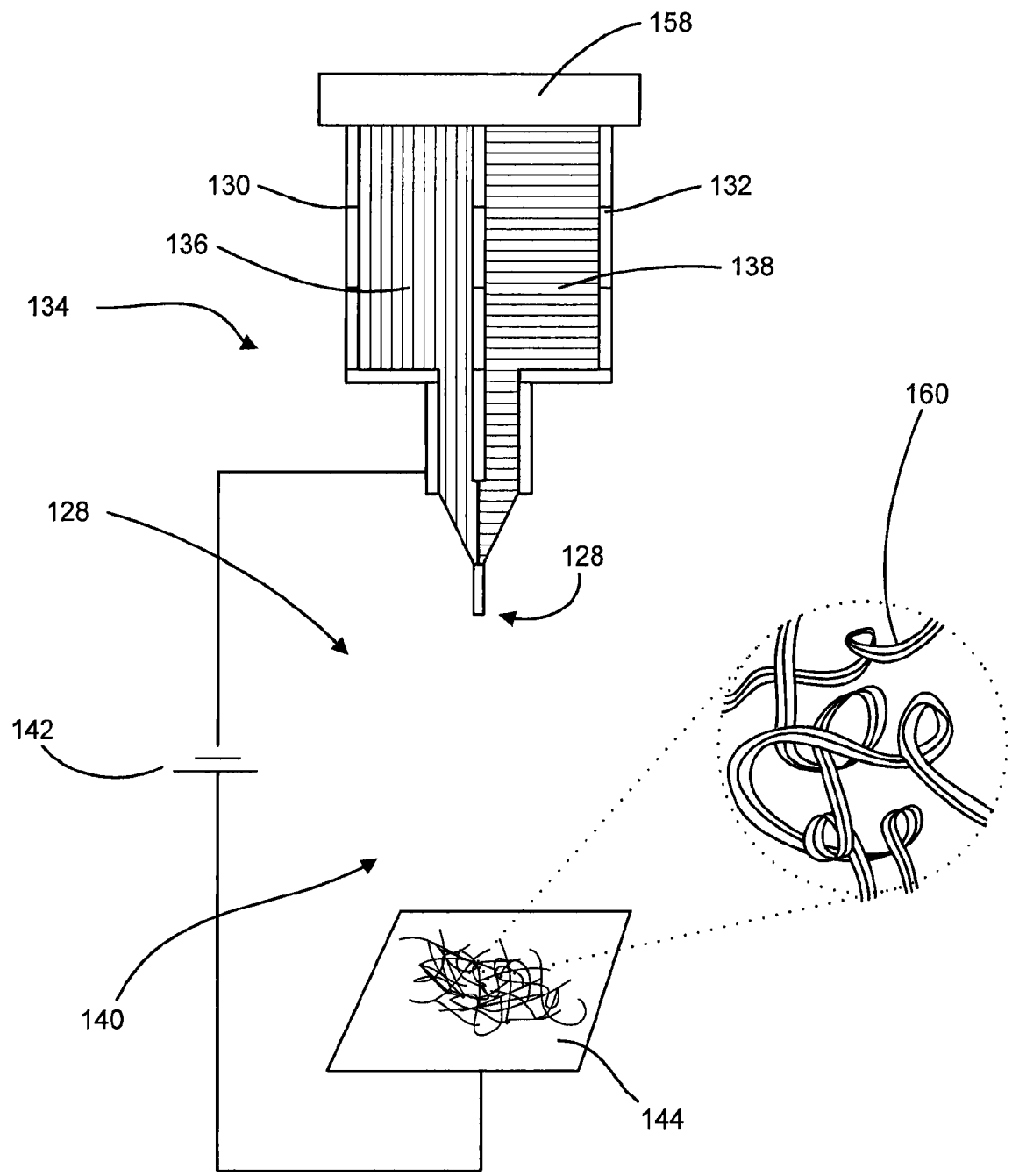
Figure 3:
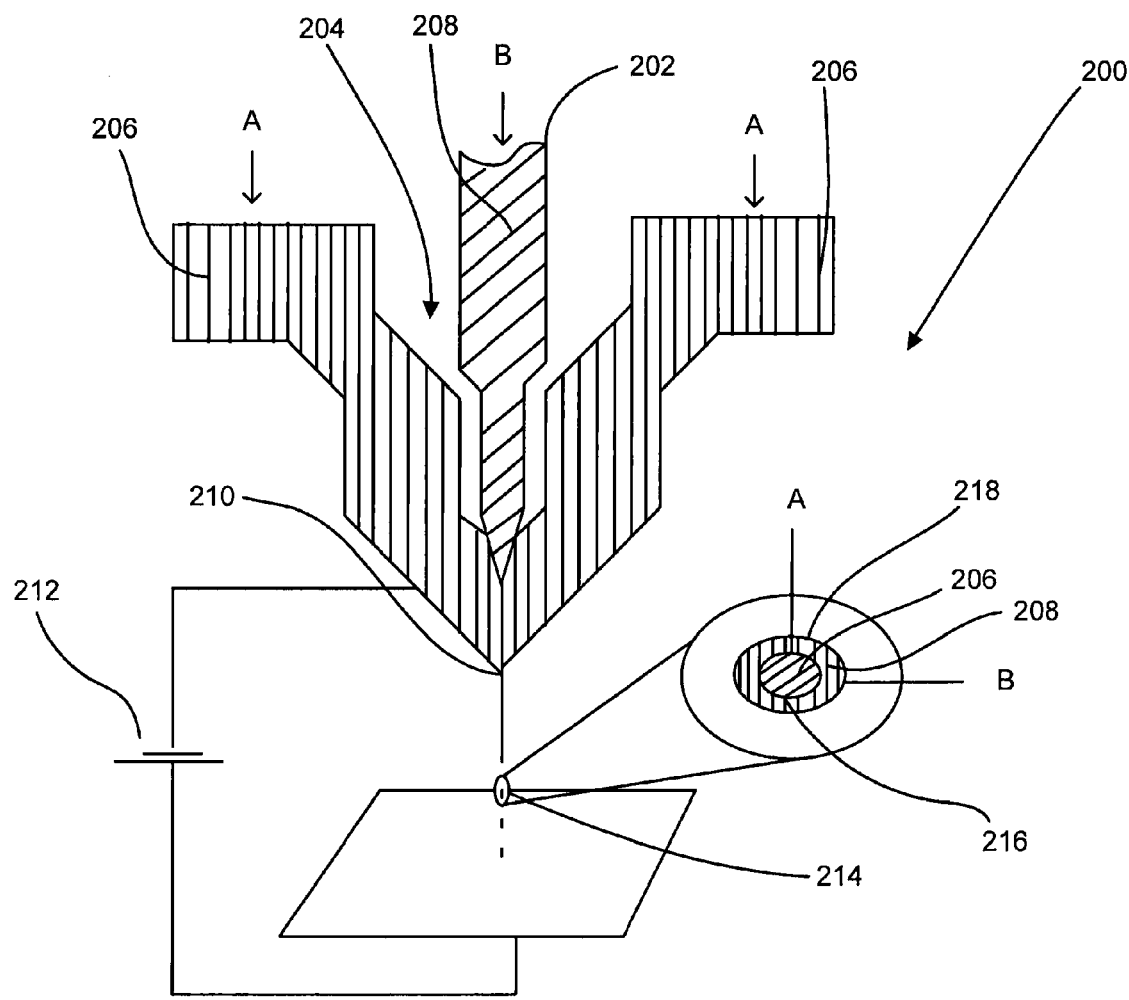
FIG. 3 shows an apparatus that forms multiphasic nanoparticle compositions in a core-and-shell configuration according to the present disclosure by electrically jetting fluid.

Suitable non-limiting polymers for use in the multiphasic compositions (e.g., in Fluid A designated 100 or Fluid B designated 102 of FIG. 2 or 3) include sodium polystyrene sulfonate (PSS), polyethers, such as a polyethylene oxide (PEO), polyoxyethylene glycol or polyethylene glycol (PEG), polyethylene imine (PEI), a biodegradable polymer such as a polylactic acid, polycaprolactone, polyglycolic acid, poly(lactide-co-glycolide polymer (PLGA), and copolymers, derivatives, and mixtures thereof. Other polymers include well known to those of skill in the art to be used in pharmaceutical, oral care, and personal care compositions, such as polyvinylpyrrolidone. Specifically, at least one phase can be designed to have one or more of the following properties based upon material selection: hydrophobic, positively-charged (cationic), negatively-charged (anionic), polyethylene glycol (PEG)-ylated, covered with a zwitterion, hydrophobic, superhydrophobic (for example having with water contact angles in excess of 150°), hydrophilic, superhydrophilic (for example, where the water contact angle is near or at 0°), olephobic/lipophobic, olephilic/lipophilic, and/or nanostructured, among others. In other aspects, one or more polymers or materials used within a phase may be functionalized to subsequently undergo reaction with various moieties or substances after formation of the multiphasic nano-component, to provide desired surface properties or to contain various moieties presented on the phase surface, as recognized by those of skill in the art.

Water-soluble and/or hydrophilic polymers, which are cosmetically and pharmaceutically acceptable, include cellulose ether polymers, including those selected from the group consisting of hydroxyl alkyl cellulose, including hydroxypropyl methyl cellulose (HPMC), hydroxypropyl cellulose (HPC), hydroxyethyl cellulose (HEC), methyl cellulose (MC), carboxymethyl cellulose (CMC), and mixtures thereof. Other polymers among those useful herein include polyvinylpyrrolidone, vinyl acetate, polyvinylpyrrolidone-vinyl acetate copolymers, polyvinyl alcohol (PVA), acrylates and polyacrylic acid (PAA), including polyacrylate polymer, vinylcaprolactam/sodium acrylate polymers, methacrylates, poly(acryl amide-co-acrylic acid) (PAAm-co-AA), vinyl acetate and crotonic acid copolymers, polyacrylamide, polyethylene phosphonate, polybutene phosphonate, polystyrene, polyvinylphosphonates, polyalkylenes, and carboxy vinyl polymer. The multiphasic compositions may comprise derivatives, copolymers, and further combinations of such polymers, as well.

Other polymers or water-soluble fillers among those useful herein include, without limitation, sodium alginate, carrageenan, xanthan gum, gum acacia, Arabic gum, guar gum, pullulan, agar, chitin, chitosan, pectin, karaya gum, locust bean gum, various polysaccharides; starches such as maltodextrin, amylose, corn starch, potato starch, rice starch, tapioca starch, pea starch, sweet potato starch, barley starch, wheat starch, modified starch (e.g., hydroxypropylated high amylose starch), dextrin, levan, elsinan and gluten; and proteins such as collagen, whey protein isolate, casein, milk protein, soy protein, keratin, and gelatin.

Further, non-limiting examples of water insoluble or hydrophobic polymers include cellulose acetate, cellulose nitrate, ethylene-vinyl acetate copolymers, vinyl acetate homopolymer, ethyl cellulose, butyl cellulose, isopropyl cellulose, shellac, hydrophobic silicone polymer (e.g., dimethylsilicone), polymethyl methacrylate (PMMA), cellulose acetate phthalate and natural or synthetic rubber; siloxanes, such as polydimethylsiloxane (PMDS), polymers insoluble in organic solvents, such as cellulose, polyethylene, polypropylene, polyesters, polyurethane and nylon, including copolymers, derivatives, and combinations thereof. The polymers may be crosslinked after formation by application of heat, actinic radiation or other methods of curing and treating polymers known to those of skill in the art.

In various aspects of the present disclosure, the polymers are present in a liquid phase prior to electrified jetting or spraying at about 0.1 to about 100% by weight (on a wet basis). While the relative concentrations of polymers in a phase can vary greatly depending on the polymer, application, and process parameters used for forming the nano-component, in certain aspects, the polymer is optionally present at about 2% to about 50% by weight; optionally from about 3% to 15% by weight of the phase.

Moreover, in certain embodiments, each phase can comprise a different moiety (e.g., each phase can be tagged with a different targeting moiety or active agent) or can optionally have different surface properties. Specifically, at least one phase can be selected to be hydrophilic, hydrophobic, positively charged (cationic), negatively charged (anionic), surface active agent modified (e.g., PEG-ylated or covered with a zwitterion), superhydrophobic, superhydrophilic, olephobic, olephilic, and/or nanostructured, as described above. An MPN phase can be designed to have such properties by providing such materials within the material forming the phase, or may be provided by subsequent treating, reacting, or coating of the exposed phase surface after formation of the MPN to achieve such properties. Polymers within a selected phase can further be modified to interact and/or react with certain target moieties. For example, reactive groups on a polymer in a first phase may be cationic and the desired moiety for the surface is anionic and will be attracted to the surface of the first phase. In other embodiments, the functional groups on the polymer may participate in a reaction with a functional group present on the moiety, such that they react and are bonded to the surface of the phase. For example, if a first phase of the MPN has a polymer with a —CHO functional group at the surface and the moiety to be attached to the first phase has a —CH$_2$NH$_2$ functional group, such groups have an affinity to form a —C=N covalent bond, thus, the surface of the first phase has an affixed moiety presented at the surface.

In various aspects, one or more exposed phase surface comprises a moiety. In certain aspects, the moiety may be provided to interact with the surrounding environment (for example, to avoid MPN detection by an immune system, provide optical properties to the MPN, provide binding to a biological or non-biological target, such as a medical device). In some aspects, the moiety is a binding moiety that provides the ability for the MPN to bind with a target. In certain aspects, the target may be an immune system cell, protein, enzyme, or other circulating agent associated with the animal). The following provides are exemplary and non-limiting examples of suitable binding moieties for use with the multiphasic nano-components of the disclosure. Proteins, such as heat shock protein HSP70 for dentritic cells and folic acid to target cancer cells. Polysaccharides or sugars, such as silyilic acid for targeting leucocytes, targeting toxins such as saporin, antibodies, including CD 2, CD 3, CD 28, T-cells, and other suitable antibodies are listed in a Table at http://www.researchd.com/rdicdabs/cdindex.htm (Jun. 14, 2007), incorporated by reference. Binding moieties include aptamers, which are small oligonucleotides that specifically bind to certain target molecules, for example, Aptamer O-7 which binds to osteoblasts; Aptamer A-10 which binds to prostate cancer cells; and Aptamer TTA1, which binds to breast cancer cells. Other exemplary binding moieties include peptides, such as CGLIIQKNEC (CLT1) and CNAGESSKNC (CLT 2) for binding to clots. Various peptides are well known in the art for binding to cells in the brain, kidneys, lungs, skin, pancreas, intestine, uterus, adrenal gland, and prostate, including those described in Pasqualini et al, "Searching for a molecular address in the brain," Mol Psychiatry. 1(6) (1996) pp. 421-2 and Rajotte, et al., "Molecular heterogeneity of the vascular endothelium revealed by in vivo phage display," J Clin Invest. 102(2) (1998) pp. 430-7, for example. Other binding biological binding moieties known or to be developed in the art are contemplated by the present disclosure.

Other conventional materials can be used to form the materials of respective phases, including solvents, plasticizers, cross-linking agents, surface active agents, fillers, bulking, or viscosity modifying agents, pH modifiers, pH buffers, anti-oxidants, impurities, UV stabilizers, and where appropriate, flavoring, or fragrance substances.

At least one phase of the multiphasic nano-component comprises an active ingredient. An active ingredient is a compound or composition that diagnoses, prevents, or treats a physiological or psychological disorder or condition, or can provide a cosmetic or aesthetic benefit. In certain aspects, an active ingredient agent is targeted to a particular target, such as organs, tissues, medical implants or devices, hair, skin, mouth, eyes, circulatory system, and the like. For example, in various aspects, the MPNs having one or more active ingredients can be used in various pharmaceutical and/or cosmetic compositions. A "pharmaceutically and/or cosmetically acceptable composition" refers to a material or combination of materials that are used with mammals or other organisms having acceptable toxicological properties for beneficial use with such an animal. Pharmaceutically and/or cosmetically acceptable compositions include drug and therapeutic compositions, oral care compositions, nutritional compositions, personal care compositions, cosmetic compositions, diagnostic compositions, and the like. In certain aspects, the pharmaceutically and/or cosmetically acceptable composition includes medical devices and implants, or surface films or coatings for such devices. Thus, in various aspects, the MPNs may be used in a wide variety of different types of compositions having a bio-functional or bio-active material and are not limited to the variations described herein. However, the present disclosure contemplates MPNs comprising one or more active ingredients that provides a diagnostic, therapeutic, prophylactic, cosmetic, sensory, and/or aesthetic benefit to an organism, such as a mammal. In certain aspects, an active ingredient prevents or treats a disease, disorder, or condition of hard or soft tissue in an organism, such as a mammal.

The ensuing description of suitable active ingredients is merely exemplary and should not be considered as limiting as to the scope of active ingredients which can be introduced into the MPNs according to the present disclosure, as all suitable active ingredients known to those of skill in the art for these various types of compositions are contemplated. Suitable active ingredients for use in such pharmaceutically and/or cosmetically acceptable compositions are well known to those of skill in the art and include, by way of example, pharmaceutical active ingredients found in the Merck Index, An Encyclopedia of Chemicals, Drugs, and Biologicals, Thirteenth Edition (2001) by Merck Research Laboratories and the International Cosmetic Ingredient Dictionary and Handbook, Tenth Ed., 2004 by Cosmetic Toiletry and Fragrance Association, each incorporated herein by reference. Each additional reference cited or described herein is hereby expressly incorporated by reference in its respective entirety. Certain suitable active ingredients, or pharmaceutically active ingredients or drugs, are known to those of skill in the art and include, but are not limited to, low-molecular weight molecules, quantum dots, natural and artificial macromolecules, such as proteins, sugars, peptides, DNA, RNA, and the like, polymers, dyes and colorants, inorganic ingredients including nanoparticles, nanomaterials, and nanocrystals, fragrances, and mixtures thereof.

A variety of low molecular weight molecules can be employed, particularly those having a molecular weight of less than about 10,000, optionally less than about 1,000, and optionally less than about 500. Such molecules include therapeutic drugs, which by way of non-limiting example includes chemotherapeutic drugs, such as doxorubicin (molecular mass of about 543.5 g/mol); paclitaxel or Taxol™ (molecular mass of about 853.9 g/mol), cholesterol lowering drug, lovastatin (molecular mass of about 404.5 g/mol), NSAID analgesic ibuprofen (molecular mass of 206.3 g/mol). Quantum dots are optically active nanostructures, for example, cadmium tellurium (CdTe). Macromolecules include a wide range of compounds, generally including polymers and biomolecules having relatively large molecular weights. Such macromolecules can be naturally occurring or synthesized. Any variety of polymers well known to those of skill in the art can be employed if the polymers are smaller than the phase in which they are distributed. Amino acids, peptides (amino acids linked via peptide bonds); polypeptides (linear chains of peptides); and proteins (primary, secondary, and tertiary folded polypeptides) are all contemplated as active ingredients. Exemplary active ingredient proteins include heat shock protein 70 (HSP70) for dentritic cells and folic acid for cancer cells. Exemplary toxins for use as active ingredients include saporin and Botulinum toxins. Exemplary sugars include silyilic acid leucocytes and glucuronic acid, for example. Useful nanoparticles and nanocrystals generally having a particles size of less than about 50 nm, optionally less than about 20 nm, and in some aspects, less than 10 nm. Useful non-limiting active ingredient nanoparticles include magnesium oxide, and metal based nano-particles, comprising gold, silver, and the like. Suitable active ingredient nanocrystals include magnetite ($Fe_3O_4$).

In other variations, the active ingredient of the MPNs of the disclosure may be used for diagnostic purposes, such as in various diagnostic medical imaging procedures (for example, radiographic imaging (x-ray), fluorescence spectroscopy, Forster/fluorescent resonance energy-transfer (FRET), computed tomography (CT scan), magnetic resonance imaging (MRI), positron emission tomography (PET), other nuclear imaging, and the like). Active ingredients for use with diagnostic imaging include contrast agents, such as barium sulfate for use with MRI, for example, or fluorescein isothiocyanate (FITC).

In other aspects, the active ingredient may provide a nutritional, cosmetic, aesthetic, or sensory benefit to the organism via the MPNs. As described above, various active ingredients are well known to those of skill in the art and include those outlined in the International Cosmetic Ingredient Dictionary and Handbook, referenced above. Various suitable active agents or ingredients are known to those of skill in the art.

In certain aspects, MPNs can be provided in pharmaceutical compositions. In certain pharmaceutical compositions, the active ingredient is provided in a suitable pharmaceutical excipient, as are well known in the art. Thus, administration of MPNs in a pharmaceutical composition can be, for example, intravenous, topical, subcutaneous, transcutaneous, intramuscular, oral, intra-joint, perenteral, peritoneal, intranasal, by inhalation, or within or coating a medical device or implant. Pharmaceutical compositions are optionally provided in the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, in unit dosage forms suitable for administration of precise dosages.

As discussed above, certain suitable active ingredients for pharmaceutical compositions or nutritional compositions, are known to those of skill in the art and include, but are not limited to, low-molecular weight molecules, quantum dots, natural macromolecules, such as proteins, sugars, peptides, DNA, RNA, and the like, artificial macromolecules, polymers, dyes and colorants, inorganic ingredients including nanomaterials and nanocrystals, fragrances, and mixtures thereof. By way of non-limiting example, the active ingredient can be a therapeutic drug that operates locally or systemically (non-localized) and may treat, prevent, or diagnose a wide variety of conditions or ailments. Active ingredients may be used to treat or prevent a disease, such as an infectious disease (a bacterial, viral, or fungal infection) or a degenerative disease (Alzheimer's, amyotrophic lateral sclerosis (ALS)). For example, active ingredients may treat an autoimmune disorder (e.g., rheumatoid arthritis, systemic lupus erythematosus (SLE), inflammatory bowel disease (IBD)), allergies, asthma, osteoarthritis, osteoporosis, cancer, diabetes, arteriosclerosis and cardiovascular disease, stroke, seizures, psychological disorders, pain, acne, caries, gingivitis, periodontitis, an $H_2$ antagonist, and the like. Various suitable active ingredients are disclosed in Merck Index, An Encyclopedia of Chemicals, Drugs, and Biologicals, Thirteenth Edition (2001) by Merck Research Laboratories and the International Cosmetic Ingredient Dictionary and Handbook, Tenth Ed., 2004 by Cosmetic Toiletry and Fragrance Association, and U.S. Pat. Nos. 6,589,562, 6,825,161, 6,063,365, and 6,491,902, all to Shefer et al.

Medical devices and/or implants, such as a stent, a pacemaker, a pacemaker lead, a defibrillator, a drug delivery device, a sensor, a pump, an embolization coil, a clip, a suture, or an electrode, by way of example, can include MPNs having an active ingredient according to the present disclosure. Exemplary medical implants include stem tissue grafts, tissue scaffolds, organ transplants, genetic therapy or stem cell therapy, among others. Where an MPN is used in an implant or in conjunction with a medical device or transplant, a variety of active ingredients can be employed to promote healing, such as promoting growth and reducing inflammation. Notwithstanding those ingredients already discussed, other active ingredients include by way of example, growth hormones and growth factors, like bone morphogenic protein (BMP) or cartilage transcription factor SRY-related HMG-box gene 9 (Sox-9)); anti-rejection drugs (such as cyclosporine), anti-inflammatory agents, analgesics, stem cell or gene therapies, or other agents that promote healing, including anti-oxidants, free radical scavengers, nutrients, co-enzymes, and other biofunctional compounds or active ingredients known or to be developed for use in such applications by those of skill in the art. Further, compositions having such active ingredients can be used in conjunction with wound dressings, gauze, films, and the like.

In other aspects, an MPN having an active ingredient can be used in an oral care composition, which can be in the form of a dentifrice, such as toothpastes, toothpowders, and prophylaxis pastes, confectioneries, including gums, beads and chews, films, paint-on products, professional polishing formulations or any other form known to one of skill in the art. Selection of specific carrier components is dependant on the desired product form, including dentifrices, toothpastes, tooth powders, prophylaxis pastes, mouth rinses, lozenges, gums, gels, paints, medicaments, and the like.

Non-limiting examples of oral care active ingredients among those useful in an MPN for use in an oral care composition include anti-plaque agents, anti-gingivitis agents, antimicrobial agents, anti-tartar agents, anti-caries agents, anti-viral agents, anti-inflammatory agents, antioxidants, whitening agents, desensitizing agents, vitamins, nutrients, natural extracts and essential oils, compatible enzymes, periodontal actives, breath freshening agents, malodor control agents, salivary stimulants, pH modifying agents, analgesics and combinations and mixtures thereof. Other oral active ingredients among those useful herein are also disclosed in U.S. Pat. No. 6,685,921 to Lawlor; U.S. Pat. No. 6,132,702 to Witt et al., and U.S. Pat. No. 5,741,138 to Rice et al.

In other aspects, multiphasic nano-components can be used in personal care compositions, such as soaps, bath gels, body washes, exfoliating scrubs, shampoos, lotions, serums, creams, sunscreens, self-tanning products, antiperspirant and deodorant products, nail care products, cosmetics, and the like. For personal care and cosmetic compositions, suitable active ingredients include anti-oxidants; free radical scavengers; moisturizers; depigmentation agents; skin lightening agents; reflectants; humectants; antimicrobial agents; antibacterial agents; allergy inhibitors; anti-acne agents; anti-aging agents; anti-wrinkling agents, antiseptics; analgesics; keratolytic agents; anti-inflammatory agents; fresheners; healing agents; anti infective agents; inflammation inhibitors; wound healing promoters; peptides, polypeptides; proteins; deodorants; antiperspirants; skin emollients; skin moisturizers; tanning agents; skin lightening agents; antifungals; depilating agents; counterirritants, non-steroidal soothing agents, anti-itch agents, poison ivy agents; poison oak agents; burn products; make-up preparations; vitamins; amino acids and their derivatives; herbal extracts; cooling agents; heating agents; skin conditioners; chelating agents; cell turnover enhancers; coloring agents; sunscreens; nourishing agents; moisture absorbers; sebum absorbers; skin penetration enhancers, pigments, dyes, fragrances, and the like, such as those disclosed in U.S. Pat. No. 6,825,161 to Shefer et al.

In alternate variations, the MPNs can be used in cleansers and/or home care compositions including powders, pastes, dishwashing liquids and automatic dishwasher detergents, fabric detergents and softeners, and hard surface cleansers. Active ingredients include enzymes, bleaching agents, surface active agents, phosphates, builders, and the like.

In certain aspects, the MPNs can be used in exemplary nutritional compositions, such as food, drinks, pills, and supplements. Suitable active ingredients include those that are nutrients, such as vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

In various aspects, an MPN delivers an effective amount of the active ingredient to a target region within an organism. An "effective" amount of an active ingredient is an amount that has a detectable effect for its intended purpose and/or benefit. Preferably, the effective amount is sufficient to have the desired therapeutic, nutritional, cleansing, aesthetic, diagnostic, and/or prophylactic effect on the target region of an organism (e.g., a mammal) to whom and/or to which the composition comprising the MPNs is administered. The specific effective amount of the active ingredient, including appropriate dosages and concentrations, will vary with such factors as the composition in which the active ingredient is provided, the site of intended delivery, the route of administration, the particular condition or subject being treated, the nature of concurrent therapy (if any), the specific active used, the specific dosage form, and the carrier employed, all of which are well known to those of skill in the art.

In certain aspects, a safe and effective amount of an active ingredient in a phase of a multiphasic nano-component is about 0.0001 to about 95 weight % of the total weight of phase (on a dry basis); optionally about 0.01 to about 90 weight %. It should be noted that where the MPN is distributed in a carrier or composition, that the overall concentration will be significantly less than in the MPN particles. In certain aspects, the active ingredient is present in a phase on an MPN at a concentration of about 0.001 to about 75% of the total phase. In other aspects, the active ingredient is present at from about 0.01 to about 20%; optionally of about 1% to about 20%; and optionally 5% to about 20%. However, as discussed above, the concentration of active ingredient is highly dependent on various factors well known to those of skill in the art, including required dosage for the target region, bioavailability of the active ingredient and the release kinetics of the phase in which the active ingredient is located, among others.

In one example, there may be two distinct target moieties on the respective phases of the MPN. A primary target is an immune system cell, such as a leukocyte or T-cell, and a secondary target is malignant cancer cell(s) within a tumor, which is the target region. The moiety on the surface of one phase/compartment of the MPN binds to the primary target cell with high selectivity (a first hemispherical phase labeled 300 in FIG. 4), while the other phase has tumor targeting moieties (a second hemisphere labeled 302 in FIG. 4). Suitable moieties for binding with targets associated with an animal include all those previously described. Thus, after delivery of the inventive MPN compositions to the target tissue, the phase of the MPN having tumor targeting moieties can bind with the secondary target (e.g., cancer) cells, once they detach from originally targeted cells. In certain aspects, a nano-component delivery system is provided for active ingredient delivery that is long-circulating, highly selective, and enables the release of multiple drugs with complex release kinetics.

Figure 4:
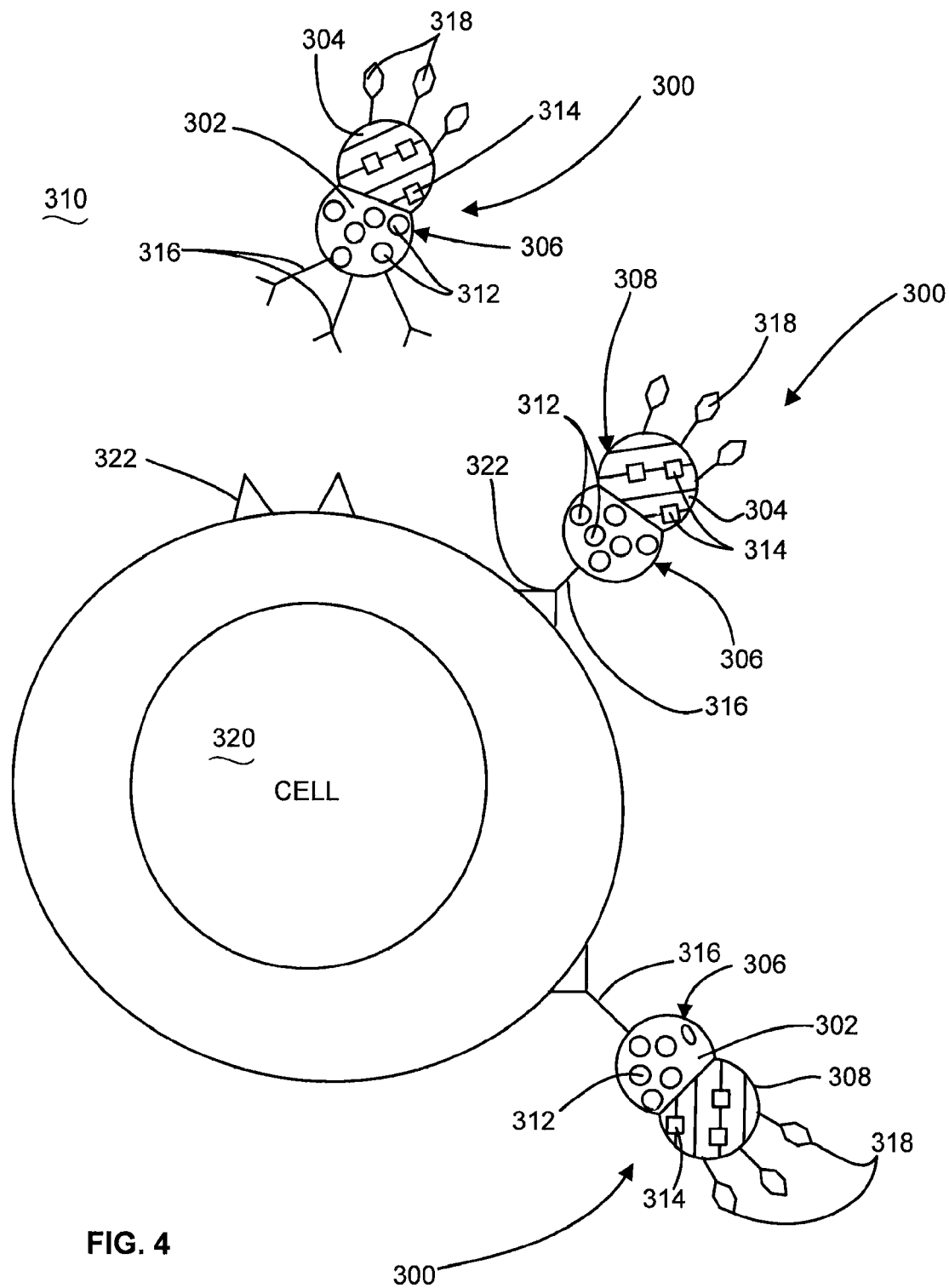
FIG. 4 is a schematic of a multiphasic nano-object composition useful for interaction with an animal's immune system in accordance with principles set forth in the present disclosure.

With reference to FIG. 4, a schematic describing the recognition of multi-functional biphasic particles to specific cell types is provided. In this illustration, a multiphasic nano-component 300 is provided within an animal. Each particle 300 includes a first phase 302 and a second phase 304, each having an exposed surface 306, 308 to an external environment 310. The first phase 302 has a first active ingredient 312 contained therein. The second phase 304 has a second active ingredient 314 contained therein. Moreover, the first phase 302 has a first binding moiety 316 at the surface 306. The second phase 304 has a second binding moiety 318 attached to the surface 308. A predetermined target 320 (here a cell) has a plurality of receptors 322. The first binding moiety 316 of the first phase 302 is complementary and binds to the receptors 322 of the target 320. The second binding moiety 318 may be compatible with a second target cell (not shown) or may provide a change in optical properties to use in conjunction with diagnostic medical imaging.

In various aspects, the multiphasic nano-components of the present disclosure provide a variety of benefits over the art. For example, the MPNs are complex and directional due to the anisotropic nanocarrier design. Conventional nano-scale delivery systems are isotropic and do not provide directional targeting. Thus, the MPNs of the present disclosure provide directed targeting based on the orientated interactions with the surrounding environment, as where conventional systems did not provide directional directed targeting. Furthermore, the MPNs of the present disclosure provide active transport rather than passive transport to target tissues, such as metastasizing tumors, by enabling transport via T-cells ("T-cell highjacking"). Only certain ligands or moieties (for example cancer ligands) are exposed, thus there is minimal risk for cross-linking or adverse interaction with the surrounding environment. Conventional delivery systems have used ligands that are permanently exposed (for extended circulation, such nanoparticles often employed polyethylene glycol), but the extended exposure of the ligands increases the potential for interaction with multiple cells. Conventional delivery systems merely provided release of multiple drugs at a single rate, however, the MPNs according to the present teachings permit release of multiple drugs at independent release rates, thus allowing complexity in the design of the release kinetics for various active ingredients. Further, MPNs prepared in accordance with the teachings of the present disclosure provide functional imaging due to two-dimensional analysis, as there is a potential to differentiate specific and non-specific events, in contrast to previous systems, where only one-dimensional imaging was possible due to contrast agents lacking the ability to undergo specific and non-specific binding.

In some aspects, it may be desirable to avoid detection by the animal's immune system, for example, to prevent removal from the body by macrophages and the like. The present disclosure contemplates various methods to prevent an animal's immune system from identifying and removing the MPN prior to delivery to the target site where the active ingredient can be delivered. For example, in certain aspects, the moieties on the surface of at least one phase include a "cloaking agent" that prevents the animal's immune system from recognizing a foreign body. Examples of such moieties include modified carbohydrates, such as sialic acid, dextran, pullulan, or glycolipids, hyaluronic acid, chitosan, polyethylene glycols, and combinations thereof. Other examples of immune system cloaking agents known in the art or to be discovered are further contemplated.

Suitable, non-limiting examples of active ingredients that can be incorporated into MPNs of the invention include the following drugs: 5-Fluorouracil (5-FU): an anti-metabolite drug commonly used in cancer treatment. Typical dosing begins with intravenous treatment at 400 mg/m$^2$ (i.e., per square meter of calculated body surface area) over 15 minutes as a bolus, then an ambulatory pump delivers 2,400 mg/m$^2$ as a continuous infusion over 46 hours. Suitable chemotherapeutic drugs can be divided into the following classes: alkylating agents, antimetabolites, anthracyclines, plant alkaloids, topoisomerase inhibitors, monoclonal antibodies, and other anti-tumor agents. In addition to the chemotherapeutic drugs described above, namely doxorubicin, paclitaxel, other suitable chemotherapy drugs include tyrosine kinase inhibitor imatinib mesylate (Gleevec® or Glivec®), cisplatin, carboplatin, oxaliplatin, mechloethamine, cyclophosphamide, chlorambucil, azathioprine, mercaptopurine, pyrimidine, vincristine, vinblastine, vinorelbine, vindesine, podophyllotoxin (L01CB), etoposide, docetaxel, topoisomerase inhibitors (L01CB and L01XX), irinotecan, topotecan, amsacrine, etoposide, etoposide phosphate, teniposide, dactinomycin, and monoclonal antibodies, such as trastuzumab (Herceptin™), cetuximab, bevacizumab and rituximab (Rituxan™), among others.

In this regard, MPNs incorporating such a drug can be designed to deliver equivalent dosages at the cancer cells, thus potentially minimizing the amount delivered generally to the patient and minimizing collateral damage to other tissues.

In certain aspects, the MPN comprises lovastatin, a cholesterol lowering and heart disease active ingredient, which can be included in at least one phase of the multiphasic nano-component compositions. In another aspect, a suitable active ingredient included in at least one phase of the MPN is Phenytoin, an anticonvulsant agent (marketed as Dilantin® in the USA and as Epanutin® in the UK by Pfizer, Inc). Antibiotics can be incorporated into one or more phases of the MPNs, such as vancomycin, which is frequently used to treat infections, including those due to methicillin resistant staph *aureus* (MRSA). At least one phase of an MPN optionally includes cyclosporin, a lipophilic drug that is an immunosuppressant agent, widely used post-allogeneic organ transplant to reduce the activity of the patient's immune system and the risk of organ rejection (marketed by Novartis under the brand names Sandimmune, the original formulation, and Neoral for the newer microemulsion formulation). MPNs comprising cyclosporine can be used in topical emulsions for treating keratoconjunctivitis sicca, as well.

In certain aspects, the MPNs of the present disclosure comprise one or more of: non-steroidal anti-inflammatory agents (NSAIDs), analgesics, COX-I and II inhibitors, and the like. For example, indomethacin is a suitable NSAID suitable for incorporation into a multiphase nano-component of the disclosure.

As described above, active ingredients can be suitable for use in a wide variety of applications and include proteins, peptides, sugars, lipids, steroids, DNA, RNA, low-molecular weight drugs. The MPN has such an active ingredient dispersed within one or more phases. For example, such active ingredients can be suspended in a polymer solution or a polymer melt. A first phase can be loaded with an active ingredient or multiple active ingredients. Likewise, a second phase can be loaded with an active ingredient or multiple active ingredients. In some embodiments, the plurality of phases may each contain one or more distinct active ingredients. The phases of the multi-phase composition can also include secondary release systems, such as nanoparticles with sizes equal or smaller than the phase, liposomes, polysomes, or dendrimers. Each of the secondary release systems can be include multiple types of active ingredients, as well, permitting a staging of release of a plurality of active ingredients. The secondary release systems can be formed with the same materials described above in the context of the multiphasic nano-components, however, can be distributed throughout a phase (for example as a continuous and discontinuous phase mixture). Thus, the secondary release system provides an additional amount of control over the release kinetics of active ingredients based and provides an even greater range of complex design and delivery options.

In certain aspects, the multiphasic nano-components are formed by electrified jetting of materials that comprise one or more polymers, such as that disclosed by Roh et al. in "Biphasic Janus Particles With Nanoscale Anisotropy", Nature Materials, Vol. 4, pp. 759-763 (October, 2005), as well as in U.S. application Ser. No. 11/272,194 filed on Nov. 10, 2005 entitled "Multiphasic Nanoparticles," and PCT Application entitled "Multiphasic Nanoparticles," also filed on Nov. 10, 2005, and in U.S. Provisional Patent Application Nos. 60/626,792 filed on Nov. 10, 2004 and 60/651,288 filed on Feb. 9, 2005, all of which are to Lahann. The contents of each of these respective references are hereby incorporated by reference in their respective entireties.

As demonstrated by FIGS. 1A and 1B in an exemplary biphasic multi-component particle, the relative volume of each respective phase can vary significantly. In FIG. 1A, the first and second phases (20, 22) of a biphasic nano-component composition is approximately 50% by volume of a first phase and 50% by volume of a second phase. However, in FIG. 1B, the first phase 20' occupies approximately 80% of the multiphasic nano-component and the second phase 22' occupies the remaining 20%. As appreciated by those of skill in the art, the relative volume and/or mass of each respective phase can be selected for various applications, depending on the desired function of each respective phase. The first phase 20' has less surface area exposed to the external medium 28 in FIG. 1B, thus the second phase 22' has a greater surface area and can provide greater exposure to materials contained on the surface or in the second phase 22'.

Electrified jetting is a process used to develop liquid jets having a nanometer-sized diameter, using electro-hydrodynamic forces. As shown in FIG. 2, a "side-by-side" configuration of Fluids A 100 and B 102 are combined to form a pendant droplet 104 of conducting liquid. The drop 104 is exposed to an electric potential 142 of a few kilovolts, where the force balance between electric field and surface tension causes the meniscus of the pendent droplet 104 to develop a conical shape, the so-called Taylor cone (not shown). Above a critical point, a highly charged liquid jet is ejected from an apex of the cone. This well-established process has been employed by two processes, i) electrospraying and ii) electrospinning.

In electrospraying, the ejected liquid jet is eventually fragmented due to instabilities and forms a spray of droplets. Among the various applications, production of charged gas phase ions of bio-macromolecules for mass spectroscopy is the most widely used. Using polymer solutions or melts as jetting liquids, electrospinning gives a way to develop fibers whose diameters are a few orders of magnitude smaller than those available from conventional spinning. Only during the last decade, electrospinning has witnessed increasing attention and nanofibers have been spun from a wide variety of polymers.

With reference to FIGS. 2A and 2B, schematics illustrating a side-by-side electrojetting apparatus implementing a variation of the method of the invention are provided. FIG. 2A is a schematic of an exemplary electrojetting apparatus where two jetting liquids are combined to form a multi-biphasic nano-component particle. FIG. 2B is a schematic of an electrojetting apparatus where two jetting liquids are combined to form biphasic fibers.

In order to incorporate two different components in each side of the composite stream 128, channels 130, 132 are configured adjacent to each other (i.e., side by side) in nozzle 134. In some variations, channels 130, 132 are capillaries. Channels 130, 132 feed two different jetting liquid streams 136, 138 into region 140 having an electric field generated by power supply 142. Channels 130, 132 are of sufficient dimensions to allow contacting of liquids streams 136, 138 to form composite stream 144. In one variation, this electric field is generated by the potential difference between nozzle 134 and plate 146. Typically, an electric field is formed by applying a potential difference between at least two electrodes from about 0.1 kV to about 25 kV. Various configurations of plates and geometries may be used to generate the electric field as known to those of skill in the art and are contemplated by the present disclosure.

FIG. 2A illustrates the electrospraying method of forming multiphasic nano-components in which particles 148 are formed. In this variation, ejected composite stream 128 is fragmented due to instabilities thereby forming a spray of droplets. FIG. 2B illustrates a variation in which nano-fibers are formed when polymer solutions or melts are used as jetting liquids, fibers 458 are obtained. In FIG. 2B a syringe pump 160 is used to drive the liquids in nozzle 134.

As schematically presented in FIGS. 2A and 2B, the biphasic jet which is ejected by the stable biphasic cone can be either fragmented to biphasic nanodroplets or can solidify into biphasic nanofibers. The two phases, i.e., the two jetting liquids (or solutions), are optionally compatible with each other (e.g., miscible or soluble) or certain variations are incompatible. Where the two polymer solutions are compatible each other, a stable cone-jet forms a stable interface between the two phases. In such situations, it is believed that the process is kinetically controlled (rather than thermodynamically controlled), resulting in one phase being trapped in each side before they mix with the other phase.

Morphological control can be achieved with the exemplary electric jetting formation methods described herein. Therefore, composite liquid stream 128 which is ejected from the pendant cone 454 can be fragmented to small droplets or sustained and elongated in the form of a continuous fiber. The size of the droplet and diameter of the fibrous jet can also be controlled. Such control is attained by changing either the material properties of jetting liquids or the working parameters of electrified jetting that breaks-up the jet stream. It should be appreciated, however, that the final morphology of the liquid jet is not always the same as those of the solid products collected on the substrates. The shape of final products can also be controlled by a sol-gel transition process or by subsequent processing after formation by electric jetting. When electric jetting is used to multiphasic nano-components in the form of fibers (for example, by electrospinning in FIG. 2B), a sol-gel transition can be intrinsic to the process, since the jetting liquids are polymer solutions or polymer melts, and solvent evaporation or a temperature drop below the thermal transition temperature during the jetting acts as a sol-gel treatment step.

Since the electrified jetting methods are related to electrohydrodynamic processes, the properties of the jetting liquid and operating parameters are interrelated. Moreover, when the jetting liquids are not one-component systems (i.e., mixtures of two or more compounds), the jetting liquid is a solution having properties governed by several parameters of the solvent and solutes. It should be appreciated that liquid properties, solution parameters, and operating parameters are related, as recognized by those of skill in the art. Relevant material properties include viscosity, surface tension, volatility, thermal and electrical conductivity, dielectric permittivity, and density. Relevant solution properties include concentrations, molecular weight, solvent mixtures, surfactants, doping agent, and cross-linking agents. Finally, relevant operating parameters include flow rate of the liquid streams, electric potential, temperature, humidity, and ambient pressure. With regard to the operating parameters, the average size and size distributions of the droplets in electrospraying with cone-jet mode seem to be dependent on the flow rate (pumping rate of the jetting liquids). At a fixed flow rate, one or several relatively monodisperse classes of nanocomponent diameters are formed. At minimum flow rate, the modality of the distributions and diameter of the droplet itself also show their minima. When the flow rate is changed, the electric field can be adjusted by changing either distance or electric potential between the electrodes in order to sustain a stable cone-jet mode. Higher flow rates may be accompanied by a higher electrical field applied for mass balance of jetting liquids. When the diameter of droplets is larger than desired, solvent evaporation does not fully occur before the droplets reach the collecting substrate, so the resulting droplets may be wet and flat.

In one aspect, the electrified jetting can be employed to create a shell and core configuration of phases. As shown in FIG. 3, a core and shell structure of MPN can be formed by an electrified jetting apparatus 200, where an injector 202 for Fluid B is disposed within an introduction region 204 for Fluid A. As Fluids A and B 206, 208 are fed to an ejection point 210 of the jetting apparatus 200, the force balance an applied electric field from a voltage source 212 and surface tension causes the meniscus of the pendent droplet 214 to develop at the Taylor cone (not shown) and to be ejected as a droplet, where Fluid A 206 is enclosed within (forms a core 216) a shell 218 of Fluid B 208. Other methods of forming such a core and shell structures include the side-by-side type of formation method described in U.S. application Ser. No. 11/272,194 filed on Nov. 10, 2005 entitled "Multiphasic Nanoparticles," and PCT Application entitled "Multiphasic Nanoparticles," also filed on Nov. 10, 2005 both to Lahann, where the surface tension of Fluids A and B, as well as the electric field application are selected to promote formation of a core and shell structure.

In various aspects, the use of the electric jetting methods of the disclosure provide greater control over the morphology and design of the nano-components as opposed to other methods of forming nano-components (such as sonication during liquid jetting and the like). For example, the liquid jetting in the presence of an electric field of the present disclosure permits the use of immiscible materials as the first and second phases, as well as miscible materials. The broad use of such materials is possible due to the rapidity of formation of particles and shapes when an electric field is applied. For many conventional methods of formation, the respective phases require immiscibility between the phases, however that is not a requirement with the electric jetting methods employed here. Further, the methods of forming the multiphasic nano-components by use of side-by-side electric jetting further provides a high degree of control over the ability to create a wide variety of shapes, including fibers and the like.

In this regard, the MPNs of the present disclosure have a wide range of controlled release and/or optical properties. Such MPNs can be designed to have pre-selected types and concentrations of active ingredients, such as cosmetic active ingredients, active ingredient drugs, fragrances and/or colorants. For example, such active ingredients can be used to dope the MPNs with additives. Any number of suitable active ingredients can be used with the MPNs. Moreover, the surface properties of each phase of the MPN can be tailored, as desired, to change the overall properties of the MPN.

Figure 5:
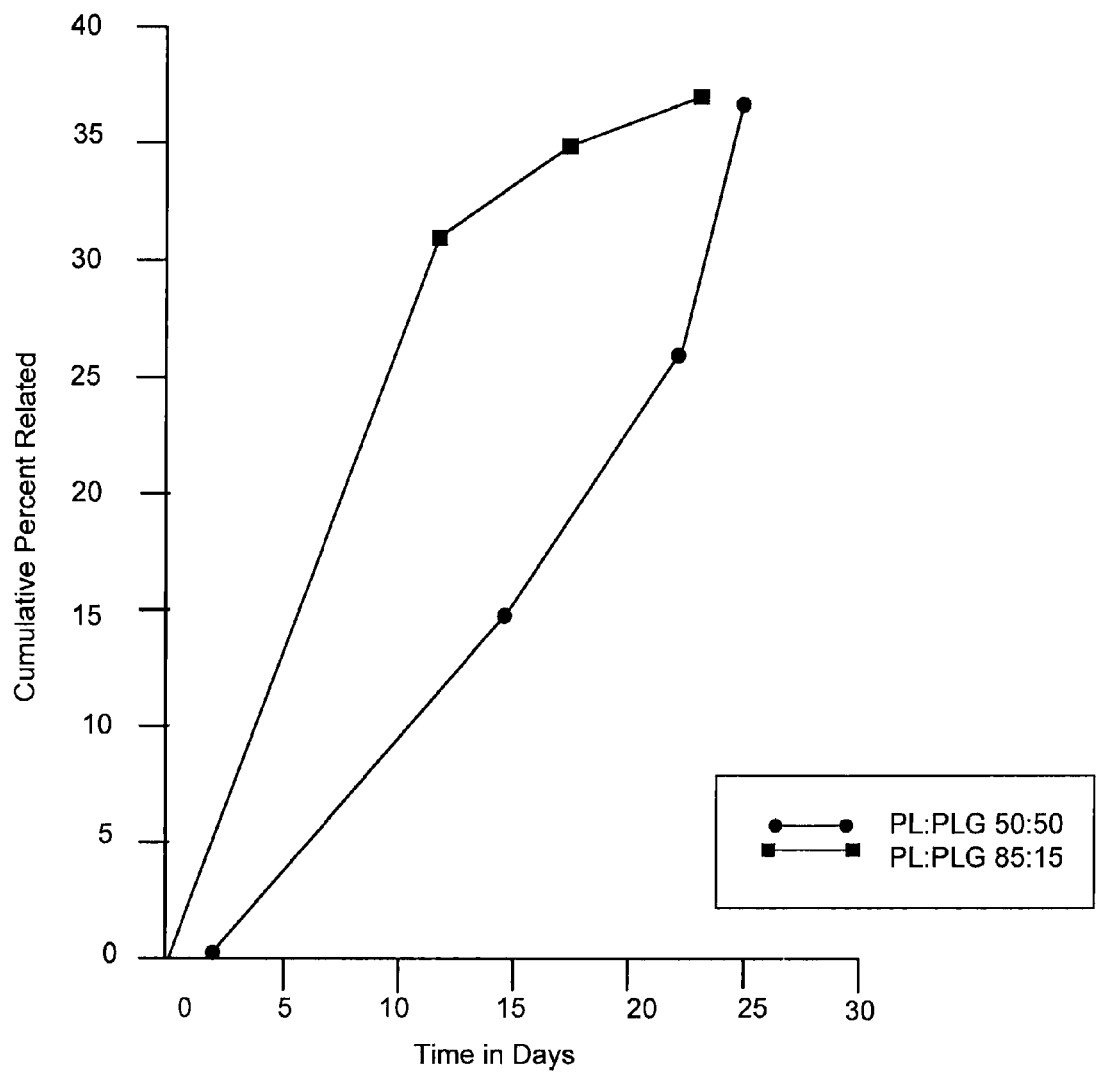
FIG. 5 is a graph showing drug delivery of a model drug lovastatin from various nanoparticles made in accordance with the present disclosure.

FIG. 5 demonstrates a model for delivery to one phase of an MPN having an active ingredient comprising lovastatin, a cholesterol-reducing/heart disease active ingredient, where the MPN is made by electrified jetting.

Multi-Stage Active Ingredient Release

Often, it is desirable to provide release of an active ingredient in different stages, which can be provided by the inventive compositions. For example, for certain conditions or disorders, such as asthma, it is desirable to release an initial high dose of a drug (such as L-Buterol) and then subsequently release the active ingredient at a slower rate for an extended time thereafter. Multiphasic nano-components according to certain aspects of the present disclosure have at least one phase that comprises a material having a higher release rate (e.g., degrades or dissolves quickly) to provide high initial doses, and comprises another phase (or phases) made of materials having a slower release rate to provide sustained release of active ingredients at lower does.

Combined Diagnostic and Therapeutic Systems

In certain aspects, multiphasic nano-components comprise different types of binding sites. In some aspects, a variety of different binding sites can be selectively presented on the surface of each respective phase. Exemplary and non-limiting binding sites can include cell receptors, peptides, proteins, amino acids, sugars, lipids, DNA, RNA, aptamers, dendrimers, azides, alkynes, and antibodies. Although any number of binding site types can be employed with MPN compositions, in certain aspects the number of types of binding sites is greater than zero and less than or equal to about twenty. In some cases, the number of binding sites is less than or equal to 5. In some cases, a single type of binding site may be provided on a phase of the multiphasic composition.

Optionally, at least one phase of an MPN comprises an active ingredient that is an indicator species, such as a colorant (e.g., pigment or dye), an imaging agent (e.g., quantum dots (which are materials for biological labeling providing high luminescence and long stability), barium or magnetite nanocrystals), or a receptor for reacting with an indicator molecule. In some aspects, a first phase of a multiphasic composition comprises a first colorant and a second phase of a multiphasic composition comprises a second colorant. In some cases, the first indicator species active ingredient in the first phase is distinct from the second indicator species active ingredient in the second phase. In certain aspects, the MPNs have anisotropic properties, thus permitting an orientation relative to a biological surface, such as the surface of a cell, a tissue or an organ. In this manner, an MPN having an indicator species can be visualized for imaging. In addition, at least one phase of the MPN can be loaded with a drug or a drug cocktail thereby enabling the MPNs to exhibit therapeutic effects, while concurrently permitting imaging.

Biomedical Coatings for Oral Care Applications.

Multiphasic nano-objects can be designed to have at least one phase exhibiting good adhesion to biological or non-biological targets. Non-limiting examples of biological targets include cells, tissue, organs, skin, hair, teeth, nails, a virus, a bacterium or a bacterial film, a bio-matrix, a plaque, an atherosclerotic deposition, and the like. Due to a high binding affinity, the biphasic nanoparticles can coat the biological targets and can provide one of the following benefits: (1) diagnosis of the biological target due to specific binding (for instance oral plaques), (2) release of drugs at the site of the biological target, (3) diagnosis combined with therapeutic release. In case of the diagnostic applications, the disclosure further provides MPNs with at least one phase that selectively binds to the biological target and at least one other phase that binds to at least one other biological target, thereby enabling a comparative interrogation of the biological environment. If for instance, in an oral imaging application, one phase binds to a plaque or caries and the other phase binds to enamel or a healthy tooth, and all phases comprise different dyes, then the plaque bio-film and/or caries can be easily imaged versus a healthy hard tissue tooth surface. In another aspect, the MPNs can be directly deposited onto the oral site using a portable and/or handheld device that fabricates biphasic nanoparticles.

Biomedical Coatings for Anti-Corrosion Applications

In certain aspects, multiphasic nano-components are designed to have at least one phase exhibiting good adhesion to metal surfaces and/or corroded metal surfaces. For example, such metal surfaces potentially include those found on an implant or medical device, such as on a stent, a pacemaker, a pacemaker lead, a defibrillator, a drug delivery device, a sensor, a pump, an embolization coil, a clip, a suture, or an electrode, by way of example. In certain aspects, due to their high binding affinity, the biphasic nanoparticles are designed to coat the metal surfaces (including those surface which may be corroded or have films). In this manner, the MPNs used in this application can be employed to diagnose or image certain regions of a metal surface due to specific binding (for instance, detecting regions of corrosion on a medical device). By way of non-limiting example, the surface of at least one phase may have the following functional groups or moieties: hydroxyl groups, siloxy groups, amine groups, phenyl groups, catechol, or combinations thereof. The MPNs can also be used to provide a biological coating of the metal surface to prevent corrosion and/or to improve the biocompatibility of the medical device surface in vivo. Similarly, in certain variations, the MPNs having a phase which reacts with a metal surface can provide both diagnosis and corrosion prevention.

Tissue Regeneration with Multiphasic Nanofibers

In certain other aspects, multiphasic nano-components in the form of nanofibers, prepared according to certain teachings of the present disclosure are deposited onto a structure, such as a scaffold, that is employed in conjunction with tissue regeneration. Each phase can be loaded with an active ingredient, which is optionally the same in each phase, or alternately different. Each phase can be selected to have similar or distinct degradation kinetics. In one aspect, at least one phase exhibits much slower degradation than the other phases, thereby enabling long-term mechanical stability, while the faster degrading phases can provide appropriate release rates for active ingredients. In another aspect, nanofibers are spun or woven using techniques known for single-phase nanofibers to make scaffolds that are made of MPNs.

In a specific aspect, a material treatment and/or surface modification is applied in only one phase of the MPN, or alternately, can be applied in only a portion of one of the phases. Such treatment and/or modification occurs to different degrees or results in different materials or materials responses. This effect can also lead to different release kinetics when different materials (forming the respective phases) are subjected to similar treatment conditions. Moreover, as described previously, each phase can be tagged with a different targeting moiety or can have different surface properties.

Any number of active agents can be used in each respective phase of the tissue regeneration device, including those active ingredients which can be suspended in a polymer solution or included in a polymer melt. Specifically, such active ingredients for tissue regeneration may include, by way of example, proteins, peptides, hormones, growth factors, sugars, lipids, steroids, DNA, RNA, low-molecular weight drugs, and the like. The respective phases can comprise the same drug, different drugs, or drug cocktails. The phases are optionally provided with secondary release systems, such as nanoparticles with sizes equal or smaller than the phase, liposomes, polysomes, or dendrimers. Each of the secondary release systems can be loaded with one or multiple types of drugs. Further, the multiphasic nano-objects are optionally loaded with multiple exclusive or generic drugs or cocktails thereof.

Topological Skin Application with Multiphasic Nanofibers and Hand-Held Devices

In other aspects, multiphasic nanofibers can be deposited onto a skin scaffold or other structure to be implanted into an organism. In accordance with the discussion above, each phase can be loaded with one or more active ingredients, which may be the same or vary between different phases. Each phase can be selected to exhibit the same or different degradation kinetics. In one aspect, at least one phase shows much slower degradation than the other phases, thereby enabling long-term mechanical stability, while the faster degrading phases can provide appropriate active ingredient release rates. In another aspect, the nanofibers are spun or woven using techniques known for single-phase nanofibers to make scaffolds that are made of MPNs.

Active ingredients are any of those discussed above that are useful in topological skin applications, including proteins, peptides, sugars, lipids, steroids, DNA, RNA, low-molecular weight drugs, or combinations thereof. Again, the respective phases optionally comprise a secondary release system, which may also release additional active ingredients.

In such variations, the nanofiber based MPNs are deposited directly onto the skin defect using a portable and/or handheld device that enables the fabrication of biphasic nanoparticles at the desired location. The portable hand-held device includes a nozzle and supply reservoirs for the respective phases. It will generally have annular electrodes, a miniaturized pump, and optionally a heating element. The materials that will form each phase can be charged into a chamber of the handheld device or may be in the form of a cartridge. The handheld device may apply heat and/or sonication to liquefy the polymer to facilitate movement, where necessary.

Multiphasic Nano-Components for Skin Care.

Multiphasic nano-components are used in personal care compositions according to certain aspects of the present disclosure, such as in skin care products, such as lotions, serums, soaps, creams, cosmetics, masks and the like. As described above, various active ingredients for skin care are well known to those of skill in the art and include those outlined above.

As described above, each phase is optionally selected to exhibit the same or different degradation kinetics. In one aspect, at least one phase shows much slower degradation than the other phases, thereby enabling long-term mechanical stability, while the faster degrading phases can provide appropriate active agent release rates. In another embodiment, the surface of at least one phase is modified to have different properties than the remainder of the phase(s) of the MPN. For example, phase surfaces can be rendered hydrophilic, hydrophobic, nanostructured, positively charged, negatively charged or comprise zwitterions, thiols, enzymes, antibodies or biological ligands, and the like. In certain aspects, an MPN can include at least one phase that is positively charged. Positively charged surfaces can be made of polyelectrolytes, such as polyamines, surfactant-like materials. A variety of positively charged materials may be employed, such as those known in the art, including those disclosed in U.S. Pat. No. 6,825,161. In another aspect, at least one phase surface is hydrophobic. Other variations of surface treatment and modification can be appreciated by the skilled artisan.

In another aspect, an MPN has at least one phase that is dynamic or changes its physical or chemical properties in response to a change in the physical, chemical, or biological environment. For instance, MPNs are created in certain aspects to have at least one phase that swells when the MPN is exposed to increased levels of moisture and/or humidity. As such, the color or other physical or chemical properties of the MPNs change or induce release of an ingredient, such as an active agent, like a drug or an enzyme, a fragrance, or a chemical, or can induce switching of the MPNs. In certain aspects, the change or response observed in the phase may be at least partially reversible, once the stimulus is taken away. Other stimuli to which MPNs can be designed to respond include light, change in pH, temperature, magnetic fields, electrical fields, or various chemicals stemming from either the human body or the environment. In yet another aspect, the MPNs are deposited directly onto the skin using a portable/handheld device that enables the fabrication of multiphasic nano-components at the site of application.

Multiphasic Nano-Components for Hair Care.

Multiphasic nano-objects are optionally used in personal care compositions, such as hair care products like shampoo, conditioner, mousse, sprays, gels, waxes, pomades, and the like. Each phase of an MPN can include the same or different ingredients. Various hair care ingredients are known to those of skill in the art, as described previously above, and include anti-oxidants, hair conditioning agents, hair dyes, pigments, radical scavengers, vitamins, fragrances, anti-bacterial agents, sunscreens, and the like. Each phase of the MPN can be selected to exhibit similar or different degradation kinetics. In one aspect, at least one phase shows much slower degradation than the other phases, thereby enabling long-term mechanical stability, while the faster degrading phases can provide appropriate drug release rates. In another variation, the surface of at least one phase is different from the remainder of the phases of the MPN. The surfaces of one or more phases of the MPN can be modified where desired to provide certain physical or chemical properties. Similar to the skin care products, MPNs can be designed to respond to and change in the presence of certain stimuli or environmental agents. In yet another embodiment, the MPNs are deposited directly onto the hair using a handheld device that enables the fabrication of biphasic nanoparticles.

The following examples are illustrative of the certain aspects of the disclosure and should not be construed as limiting to the scope of the disclosure.

EXAMPLE 1

Biphasic Jetting

The experimental setup for the present experiment conforms to that of FIG. 2. Two jetting liquids (Fluid A and Fluid B) are fed using a dual syringe applicator assembly (FibriJet® SA-0100, Micromedics, Inc., MN, USA). In this setup, two 1 ml syringes are controlled by one syringe pump. Each syringe is filled with separate jetting solutions. These two syringes are connected to a dual channel tip (Fibrikf SA-0105, Micromedics, Inc., MN, USA) which has a dual cannula with a dimension of 26 gauge and 3 inch length. These dual cannula or capillaries are covered with a transparent plastic tube that ties these two capillaries in side-by-side fashion. In order to avoid the capillary pressure caused by the groove between the two round shape cannula and create a stable biphasic pendent droplet from the side-by-side capillary setup, the tip end level is made even by the sharp cutting of the two capillaries and the plastic tube.

In this example, the material properties of Fluid A and Fluid B (both liquids) are similar. Compatibility between the two jetting solutions is desirable to achieve a stable interface between the two phases, and basic components (i.e., polymer and solvent) can be the same to achieve similar viscosity, surface tension, and the like. However, each side includes a different active ingredient that is maintained in each phase throughout the process. Preventing diffusion of these different active ingredients between phases (from one phase to the other) is usually avoided until the point of solidification. In line with the above mentioned objectives, mixtures of PEO as a polymer and an active ingredient comprising Cyclosporin, suspended in water, is selected as active ingredient for each side of the jetting solution. PEO (average molecular weight 600,000) is purchased from Aldrich Co. (USA). Jetting is performed with solutions which are composed of 8% of polyacrylic acid and 1% of Cyclosporin by weight in Fluid A and 10% of poly(acrylic acid-co-polyacrylamide) and 1% of Cyclosporin by weight in Fluid B for the second organic jetting solution.

8 kV of electric potential is applied between 25 cm separation of the electrodes. A glass slide is covered with aluminum foil except about 80% of the surface of one face, and the jetting is performed on the open face of the glass slide. Electrodes are connected directly to the side-by-side capillaries and the aluminum foil covering the glass slide substrate. A flow rate of 0.1 ml/hour is set for each side. A beads-on-string morphology is generated.

EXAMPLE 2

Core and Shell Formation

In this example, Fluid A and Fluid B are delivered in a configuration shown in FIG. 3. Fluid A comprises a poly (lactide-co-glycolide polymer (PLGA) in a solvent system comprising acetonitrile and water. Fluid B comprises an aqueous emulsion containing a lipophilic active ingredient, Cyclosporin, suspended in water. The fluids are processed under similar conditions described in Example 1. Fluid B becomes a core containing a lipophilic active ingredient and Fluid A becomes a shell surrounding Fluid B that is hydrophilic. In this regard, a nanoparticle composition is formed that can be introduced to an animal. The PLGA dissolves in vivo exposing the lipophilic active ingredient within the body for bioavailability and delivery. The nanoparticle provides for delivery and bioavailability of an otherwise difficult-to-deliver lipophilic active ingredient.

EXAMPLE 3

Multi-Stage Drug Delivery

In Example 3, conventional jetting solutions are prepared by dissolving 50 mg of a PLGA polymer system with variable ratio of PLA (polylactide) and PGA (polyglycolic acid) (commercially available from Polysciences, Inc of Warrington, Pa.) and 5 mg of Doxorubicin hydrochloride in 1 ml of chloroform. Ratios of PLA:PGA can range from 10:1 to 1:10, for example 1:1 and 3:1. Doxorubicin is commercially available from Sigma-Aldrich (98%, D1515), Fluka (>98%, 44583) or Spectrum Chemicals. The solutions are stirred thoroughly until all the polymer and drug are completely dissolved in chloroform. Jetting solutions are filled in 1 ml syringes (Becton, Dickinson and Company, NJ, USA). The flow rate is controlled by a syringe pump in a range of 10-100 μl/min. A conducting single capillary (Precision stainless steel tips, 26 gauge, 0.5 inch long, EFD Inc., RI, USA) is connected via the tip of the syringe and further attached to the cathode of the high voltage supply (ES30P, Gamma High Voltage Research Inc., FL. USA). The electron voltage is controlled in the range of 5-15 kV. A square piece of aluminum foil is used as counterelectrode and is connected to the ground.

To fabricate biphasic nanoparticles with anti-cancer activity, 10 mg of Doxorubicin hydrochloride is loaded in multiphasic PLGA particles created in accordance with the principles of the present disclosure and suspended in 0.975 ml of phosphate buffered saline (PBS, pH 7.4). Microtubes containing this suspension are kept on a shaker at 60 rpm at room temperature during the release experiment. Initially, particles are dispersed by use of tip-type sonicator (Agilent Technologies, Inc., USA) followed by centrifugation. The concentration of drug in supernatant solution is determined by use of UV spectrometer (Cole-Parmer, Inc., USA). In the case of the model drug Doxorubicin hydrochloride, a characteristic maximum UV absorbance at 234 nm can be used to determine concentrations. Moreover, the drug is fluorescent and emits at 410 nm. Analogue calibration curves were obtained for all drugs studied for release. In certain aspects, one or more phases may contain a ligand that interacts with the host animal's immune system, such as antibodies, folic acid, or other ligands known to those of skill in the art.

In vitro drug release experiments to demonstrate release of Lovastatin from PLGA nanoparticles made by electrified jetting such as those polymer systems described in the context of Doxorubicin above. Release kinetics for Lovastatin from nanoparticles are assessed with two different polymer matrices, as shown in FIG. 5.

EXAMPLE 4

MPNs Having Charged Surfaces

An aqueous solution of 95 weight % polyethylene imine (PEI), and 5 wt. % poly(acryl amide-co-acrylic acid) (PAAm-co-AA) is co-jetted with an aqueous solution of 95 wt. % poly(acrylic acid) (PAA) and 5 wt. % PEI. Each respective solution is loaded with a different colorant (dye), for example, one colorant may be selected to be dextran and another fluorescein isothiocyanate (FITC). Two parallel polymer flows are introduced in a nozzle that contains inlets in a side-by-side geometry, such as is shown in FIG. 2A. Under these conditions, a droplet forms at the tip of the nozzle. Upon application of a sufficiently strong electrical field (about 5 to about 10 kW) between the nozzle and a counterelectrode, which serves as the collector, a polymer thread is ejected from the droplet resulting in biphasic nanoparticles, where one phase is predominately positively charged and the other phase is predominately negatively charged.

EXAMPLE 5

Multiphasic Disk-Shaped MPNs

A solution of 5 wt. % poly(lactide-co-glycolide polymer (PLGA) in chloroform is co-jetted with a solution of 5 wt. % PLGA in chloroform. Two parallel polymer flows are introduced in a nozzle with the configuration described above for Example 4 (side-by-side geometry). Under these conditions, a droplet forms at the tip of the nozzle. Upon application of a sufficiently strong electrical field between the nozzle and a counterelectrode, which serves as the collector, a polymer thread is ejected from the droplet resulting in biphasic disks with one phase predominately comprising PLGA (50:50) and the other phase predominately comprising PLGA (85:15).

EXAMPLE 6

Dual Protein Delivery MPNs

A solution of 5 wt. % polyethylene oxide (PEO) (100 kD) and bone morphogenetic protein (BMP-2) in water is co-jetted with a solution of 5 wt. % PEO (100 kD) and transcription factor SRY-related HMG-box gene 9 (Sox-9). The protein content can vary between about 0.01 to about 25% relative to PEO. Two parallel polymer flows are introduced in a nozzle that contains to inlets in a side-by-side geometry, as described above in Example 4. A polymer thread is ejected from the droplet resulting in biphasic disks with one phase having BMP-2 as an active ingredient and the other phase including Sox-9 as an active ingredient. The controlled delivery of the proteins facilitates specific tissue formation: BMP-2 (bone) and Sox-9 (cartilage).

EXAMPLE 7

Magnetic MPNs for MRI Imaging

An aqueous solution of 95 wt. % PAA and 5 wt. % PAAm-co-AA is co-jetted with an aqueous solution of PAAm-coAA which comprises an active ingredient including magnetite nanocrystals homogeneously suspended in the polymer solution. The content of the magnetite nanocrystals can vary from about 0.05 to about 25 wt. % relative to PAAm-co-AA. Two parallel polymer flows are introduced in a nozzle that contains to inlets in a side-by-side geometry, as described above in Example 4. A biphasic nano-component with magnetite nanocrystals as the active ingredient in one phase is formed. These nano-component particles show a clear response to application of a magnetic field. Thus, such MPNs can be employed in conjunction with magnetic resonance imaging (MRI) for medical diagnosis applications.

EXAMPLE 8

Protein Containing MPNs

An aqueous solution of 95 wt. % PAA and 5 wt. % PAAm-co-AA is co-jetted with an aqueous solution of PAAm-coAA which also contains PEO at about 0.05 to about 75 wt % relative to PAAm-co-AA. The PEO contains vascular endothelial growth factor (VEGF) as an active ingredient, at a concentration of about 0.1 to about 20 wt. % relative to PEO. A side-by-side jetting apparatus is used, as described above in Example 4. Biphasic nano-component particles having PEO and VEGF protein in one phase are created. In this manner, the VEGF biological function is preserved during the formation process and after storage for several weeks.

EXAMPLE 9

Protein Containing MPNs

An aqueous solution 5 wt. % of PAAm-co-AA is co-jetted with an aqueous solution of 10 wt. % of a mixture of polyaniline (PA), PEO, and sodium chloride. PEO content ranges from about 0.05 to about 75 wt. % relative to PAA and sodium chloride is present around 1 wt. %. The PEO contains vascular endothelial growth factor (VEGF) as an active ingredient, at a concentration of about 0.1 to about 20 wt. % relative to PEO. A side-by-side jetting apparatus is used to form core-and-shell particles. Biphasic core-and-shell nano-component particles having PEO and VEGF protein in one phase are created. The particles consist of a PEO/PAA/VEGF (protein) core and a PAAm-co-AA shell. In this manner, the VEGF biological function is preserved during the formation process and after storage for several weeks.

EXAMPLE 10

Hydrophobic/Hydrophilic MPNs

A solution of 5 wt. % PLGA in chloroform is co-jetted with a solution of 5 wt. % PLGA in chloroform and a polylactic acid (PLA) having (on average) at least one acetylene group per molecule. A side-by-side jetting apparatus is used, as described above in Example 4. Biphasic disks form where one phase has PLGA (50:50) and the other phase has PLGA (85:15) with acetylene-modified PLA. A functionalized surface is provided for one phase by subsequent reaction/conversion of acetylene with an azide-polyoxyethylene glycol (Azide-PEG) ligand, which results in PEG-ylation of a surface (a hemisphere) of the biphasic nanoparticles, providing the functionalized side with hydrophilic properties and the PLGA phase with hydrophobic properties.

EXAMPLE 11

Hydrophobic/Hydrophilic MPNs

A solution of 5 wt. % polydimethylsiloxane (PMDS) in chloroform is co-jetted with an aqueous solution of 5 wt. % of collagen containing basic fibroblast growth factor (BFGF) as the active ingredient. The forming apparatus is the same as that discussed above for Example 4. Biphasic nano-component disks are formed where one phase comprises hydrophobic PDMS and the other phase comprises collagen/BFGF. The MPNs can be used in various applications, such as for sprayable wound coverage.

EXAMPLE 12

Hydrophobic/Hydrophilic MPNs

A solution of 5 wt. % polydimethylsiloxane (PMDS) in chloroform is co-jetted with an aqueous solution of 5 wt. % of collagen containing an active ingredient comprising genetically-modified adenovirus. The forming apparatus is the same as that discussed above for Example 4. Biphasic nano-component disks are formed with one phase comprising PDMS (hydrophobic) and the other phase having collagen and the adenovirus. Such MPNs can be used for transfection of cells in the context of gene therapy.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A multiphasic nano-component comprising a first phase and at least one additional phase that is compositionally distinct from said first phase, wherein said first phase defines a first spatially discrete compartment of the nano-component and said at least one additional phase defines a second spatially discrete compartment, wherein said first phase and said at least one additional phase are oriented in the nano-component to provide an anisotropic morphology so that said first compartment and said second compartment have a side-by-side orientation and said first phase and said at least one additional phase each have an exposed surface, wherein at least one of said first phase and said additional phase comprises a pharmaceutically and/or cosmetically acceptable polymer, and wherein at least one of said first phase and said additional phase comprises an active ingredient.

2. The multiphasic nano-component according to claim 1, wherein said first phase comprises a first active ingredient and said at least one additional phase comprises a second active ingredient.

3. The multiphasic nano-component according to claim 1, wherein said first phase comprises a first component that is hydrophobic and a second component present in said at least one additional phase is hydrophilic.

4. The multiphasic nano-component according to claim 1, wherein at least one of said exposed surfaces comprises a moiety for binding to a target associated with an animal.

5. The multiphasic nano-component according to claim 4, wherein said moiety is selected from the group: proteins, peptides, polysaccharides, sugars, toxins, antibodies, aptamers, and combinations thereof.

6. The multiphasic nano-component according to claim 1, wherein at least one of said exposed surfaces is treated after formation of the nano-component to modify the chemical or physical characteristics of said surface.

7. The multiphasic nano-component according to claim 1, wherein said first active ingredient has a first charge and a second component present in said at least one additional phase has a second charge opposite to said first charge.

8. The multiphasic nano-component according to claim 1, wherein said first phase is hydrophobic and said at least one additional phase is hydrophilic.

9. The multiphasic nano-component according to claim 1, wherein said active ingredient is selected from the group consisting of: a therapeutic active ingredient, a systemic active ingredient, a chemotherapy active ingredient, a localized active ingredient, an oral care active ingredient, a nutritional active ingredient, a personal care active ingredient, a cosmetic active ingredient, a diagnostic imaging indicator agent, and combinations thereof.

10. The multiphasic nano-component according to claim 1, wherein said nano-component is formed by an electrified jetting process and has a shape selected from the group consisting of: spheres, rectangles, polygons, disks, toroids, cones, pyramids, rods, cylinders, and fibers.

11. The multiphasic nano-component according to claim 1, wherein the pharmaceutically and/or cosmetically acceptable polymer comprises a polymer selected from the group consisting of: biodegradable polymers, water soluble polymers, water dispersible polymers, water insoluble polymers, and combinations and co-polymers thereof.

12. The multiphasic nano-component according to claim 1, wherein an amount of active ingredient present in said first phase is about 0.01% to about 90% by weight of the first phase.

13. The multiphasic nano-component according to claim 12, wherein said at least one additional phase further comprises a second active ingredient present at about 0.01% to about 90% by weight of said additional phase.

14. The multiphasic nano-component according to claim 1, wherein the pharmaceutically and/or cosmetically acceptable polymer is selected from the group consisting of: sodium polystyrene sulfonate (PSS), polyethers, polyethylene oxide (PEO), polyethylene imine (PEI), polylactic acid, polycaprolactone, polyglycolic acid, poly(lactide-co-glycolide polymer (PLGA), polyvinylpyrrolidone, hydroxyl alkyl cellulose, hydroxypropyl methyl cellulose (HPMC), hydroxypropyl cellulose (HPC), hydroxyethyl cellulose (HEC), methyl cellulose (MC), carboxymethyl cellulose (CMC), vinyl acetate, polyvinylpyrrolidone-vinyl acetate copolymers, polyvinyl alcohol (PVA), polyacrylates, polyacrylic acid (PAA), vinylcaprolactam/sodium acrylate polymers, methacrylates, poly(acryl amide-co-acrylic acid) (PAAm-co-AA), vinyl acetate, crotonic acid copolymers, polyacrylamide, polyethylene phosphonate, polybutene phosphonate, polystyrenes, polyvinylphosphonates, polyalkylenes, carboxy vinyl polymer, cellulose acetate, cellulose nitrate, ethylene-vinyl acetate copolymers, vinyl acetate homopolymers, ethyl cellulose, butyl cellulose, isopropyl cellulose, shellac, siloxanes, polydimethylsiloxane, polymethyl methacrylate (PMMA), cellulose acetate phthalate, natural or synthetic rubber; cellulose, polyethylene, polypropylene, polyesters, polyurethane, nylon, and copolymers, derivatives, and mixtures thereof.

15. The multiphasic nano-component according to claim 1, wherein the active ingredient is selected from the group consisting of: low-molecular weight molecules, quantum dots, natural and artificial macromolecules, proteins, sugars, peptides, polypeptides, proteins, amino acids, enzymes, DNA, RNA, polymers, nanoparticles, nanocrystals, growth hormones, growth factors, anti-rejection drugs, anti-inflammatory agents, analgesics, stem cell therapy agents, gene therapy agents, anti-oxidants, free radical scavengers, nutrients, co-enzymes, systemic drugs, therapeutic drugs, localized drugs, tooth whitening agents, skin whitening agents, antimicrobial agents, antibacterial agents, antibiotics, antifungal agents, anti-caries agents, anti-tartar agents, anti-plaque agents, anti-adhesion agents, desensitizing agents, anti-inflammatory agents, malodor control agents, flavoring agents, anti-aging agents, salivary stimulants, periodontal actives, depigmentation agents, skin lightening agents, reflectants, humectants, allergy inhibitors, anti-acne agents, anti-aging agents, anti-wrinkling agents, antiseptics, keratolytic agents, fresheners, healing agents, inflammation inhibitors, wound healing promoters, deodorants, antiperspirants, skin emollients, tanning agents, antifungals, depilating agents, counterirritants, nonsteroidal soothing agents, anti-itch agents, poison ivy agents, poison oak agents, burn products, vitamins, cooling agents, heating agents, chelating agents, anti-psoriasis agents, anti-dandruff agents, skin conditioners, moisturizing agents, emollients, humectants, occlusive agents, skin lipid fluidizers, deodorant active agents, antiperspirant active agents, skin and/or scalp sensates, skin and/or scalp soothing and/or healing agents, astringents, opacifying agents, biocides, natural and synthetic extracts and essential oils, nutrients, enzymes, proteins, amino acids, vitamins, analgesics, sunscreen agents, UV absorbers, antioxidants, antibiotics, exfoliants, cell turnover enhancers, coloring agents, sunscreens, nourishing agents, moisture absorbers, sebum absorbers, skin penetration enhancers, colorants, pigments, dyes, flavors, fragrances, and combinations thereof.

16. The multiphasic nano-component according to claim 1, wherein said first phase comprises a cationic component that is positively charged and an anionic component present is in said at least one additional phase that is negatively charged.

17. A multiphasic nano-component comprising a first phase and at least one additional phase that is compositionally distinct from said first phase, wherein said first phase defines a first spatially discrete compartment of the nano-component and said at least one additional phase defines a second spatially discrete distinct compartment of the nano-component, wherein said first phase and said at least one additional phase are oriented in the nano-component to provide an anisotropic morphology so that said first compartment and said second compartment have a side-by-side orientation and said first phase and said at least one additional phase each have an exposed surface, wherein said first phase comprises a first pharmaceutically and/or cosmetically acceptable polymer and said additional phase comprises a second distinct pharmaceutically and/or cosmetically acceptable polymer, and wherein at least one of said first phase and said additional phase comprises an active ingredient.

18. The multiphasic nano-component according to claim 17, wherein said first phase comprises a first active ingredient and said at least one additional phase comprises a second active ingredient distinct from said first active ingredient.

* * * * *

UNITED STATES PATENT AND TRADEMARK OFFICE
CERTIFICATE OF CORRECTION

PATENT NO. : 8,241,651 B2
APPLICATION NO. : 11/763842
DATED : August 14, 2012
INVENTOR(S) : Joerg Lahann It is certified that error appears in the above-identified patent and that said Letters Patent is hereby corrected as shown below:

In the Specifications:

| | |
|---|---|
| Column 1, line 59 | Before "the animal" insert --with--. |
| Column 2, line 28 | "shows" should be --show--. |
| Column 3, line 50 | "have" should be --having--. |
| Column 6, line 37 | "In a certain aspects" should be --In certain aspects--. |
| Column 6, line 41 | "materials responses" should be --material responses--. |
| Column 7, line 10 | "(PLGA)," should be --(PLGA)),--. |
| Column 8, line 53 | After "provides" delete "are". |
| Column 15, line 48 | "can be include" should be --can include--. |
| Column 16, line 59 | "liquids streams" should be --liquid streams--. |
| Column 17, lines 15-16 | After "compatible" insert --with--. |
| Column 18, line 13 | "balance" should be --balances--. |
| Column 19, line 4 | "lower does" should be --lower doses--. |
| Column 19, line 24 | "nanocrystals)," should be --nanocrystals)),--. |
| Column 20, line 5 | "surface" should be --surfaces--. |
| Column 20, lines 39-40 | "materials responses" should be --material responses--. |
| Column 24, line 44 | "(PLGA)" should be --(PLGA))--. |
| Column 24, line 65 | "contains to inlets" should be --contains two inlets--. |
| Column 25, lines 16-17 | "contains to inlets" should be --contains two inlets--. |
| Column 25, line 45 | After "solution" insert --of--. |

Signed and Sealed this
Twenty-first Day of May, 2013

Teresa Stanek Rea
*Acting Director of the United States Patent and Trademark Office*